United States Patent
Hagadorn et al.

(10) Patent No.: US 10,208,140 B2
(45) Date of Patent: *Feb. 19, 2019

(54) QUINOLINYLDIAMIDO TRANSITION METAL COMPLEXES, PRODUCTION AND USE THEREOF

(71) Applicant: ExxonMobil Chemical Patents Inc., Baytown, TX (US)

(72) Inventors: John R. Hagadorn, Houston, TX (US); Patrick J. Palafox, Hattiesburg, MS (US); Peijun Jiang, League City, TX (US); Yaohua Gao, Houston, TX (US); Xin Chen, Humble, TX (US); Georgy P. Goryunov, Kokoshkino (RU); Mikhail I. Sharikov, Moscow (RU); Dmitry V. Uborsky, Moscow (RU); Alexander Z. Voskoboynikov, Moscow (RU)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/629,586

(22) Filed: Jun. 21, 2017

(65) Prior Publication Data

US 2018/0002352 A1 Jan. 4, 2018

Related U.S. Application Data

(60) Provisional application No. 62/357,033, filed on Jun. 30, 2016.

(51) Int. Cl.
 *C08F 10/06* (2006.01)
 *C08F 10/02* (2006.01)
 *C07F 7/00* (2006.01)

(52) U.S. Cl.
 CPC ............ *C08F 10/06* (2013.01); *C07F 7/003* (2013.01); *C08F 10/02* (2013.01)

(58) Field of Classification Search
 None
 See application file for complete search history.

(56) References Cited

U.S. PATENT DOCUMENTS

| | | | |
|---|---|---|---|
| 6,103,657 | A | 8/2000 | Murray |
| 6,175,409 | B1 | 1/2001 | Nielsen et al. |
| 6,260,407 | B1 | 7/2001 | Petro et al. |
| 6,294,388 | B1 | 9/2001 | Petro |
| 6,306,658 | B1 | 10/2001 | Turner et al. |
| 6,406,632 | B1 | 6/2002 | Safir et al. |
| 6,436,292 | B1 | 8/2002 | Petro |

(Continued)

FOREIGN PATENT DOCUMENTS

| | | |
|---|---|---|
| WO | 00/09255 | 2/2000 |
| WO | 2007/035492 | 3/2007 |
| WO | 2014/123683 | 8/2014 |

OTHER PUBLICATIONS

Zhang et al., "Synthesis and Computation of Diastereomeric Phenanthroline-quinine Ligands and Their Application in Asymmetric Henry Reaction," Tetrahedron, 2013, vol. 69, No. 49, pp. 10644-10652.

(Continued)

*Primary Examiner* — Catherine S Branch

(57) ABSTRACT

Quinolinyldiamido transition metal complexes are disclosed for use in alkene polymerization to produce multimodal polyolefins.

44 Claims, 4 Drawing Sheets

(56) References Cited

U.S. PATENT DOCUMENTS

| | | | |
|---|---|---|---|
| 6,454,947 | B1 | 9/2002 | Safir et al. |
| 6,455,316 | B1 | 9/2002 | Turner et al. |
| 6,461,515 | B1 | 10/2002 | Safir et al. |
| 6,475,391 | B2 | 11/2002 | Safir et al. |
| 6,489,168 | B1 | 12/2002 | Wang et al. |
| 6,491,816 | B2 | 12/2002 | Petro |
| 6,491,823 | B1 | 12/2002 | Safir et al. |
| 6,900,321 | B2 | 5/2005 | Boussie et al. |
| 6,953,764 | B2 | 10/2005 | Frazier et al. |
| 7,317,057 | B2 | 1/2008 | Solan et al. |
| 7,858,718 | B1 | 12/2010 | Nagy et al. |
| 7,973,116 | B2 | 7/2011 | Hagadorn et al. |
| 8,049,015 | B2 | 11/2011 | Hutchinson et al. |
| 8,158,733 | B2 | 4/2012 | Nagy et al. |
| 8,362,162 | B2 | 1/2013 | Hustad et al. |
| 9,290,519 | B2 | 3/2016 | Hagadorn et al. |
| 2012/0016092 | A1 | 1/2012 | Nagy et al. |
| 2016/0013431 | A1 | 1/2016 | Choi et al. |
| 2018/0002352 | A1 | 1/2018 | Hagadorn et al. |
| 2018/0134816 | A1 | 5/2018 | Canich et al. |
| 2018/0134827 | A1 | 5/2018 | Hagadorn et al. |

OTHER PUBLICATIONS

Hu et al., Syntheses, Characterization, and Ethylene Polymerization of Titanium Complexes with Double-Duty Tridentate [ONN] Ligands, Organometallics, 2012, vol. 31, p. 3241.

Nifant'Ev et al., "Reaction if 2,8-Bis(o-hydroxyaryl)quinolones with Group 4 Metal Alkyls Resulting in Three Distinct Coordination Modes of the Tridentate Ligand . X-ray Structure of Complexes and Performance as Precursors in Ethylene Polymerization Catalysis," Organometallics, 2013, vol. 32, No. 9, pp. 2685-2692.

Nifant'Ev et al., "Zirconium and Hafnium Complexes based on 2-aryl-8-arylaminoquinoline Ligands: Synthesis, Molecular Structure, and Catalytic Performance in Ethylene Copolymerization," Dalton Transactions, 2013, vol. 42, No. 5, pp. 1501-1511.

Froese et al., "Mechanism of Activation of a Hafnium Pyridyl-Amide Olefin Polymerization Catalyst: Ligand Modification by Monomer," Journal of American Chemical Society, 2007, vol. 129, No. 25, pp. 7831-7840.

Boussie et al., "A Fully Integrated High-Throughput Screening Methodology for the Discovery of New Polyolefin Catalysts: Discovery of a New Class of High Temperature Single-Site Group (IV) Copolymerization Catalysts." Journal of American Chemical Society, 2002, vol. 125, No. 14, pp. 4306-4317.

U.S. Appl. No. 15/869,941, filed Jan. 12, 2018.

U.S. Appl. No. 15/906,861, filed Feb. 28, 2018.

QUINOLINYLDIAMIDO TRANSITION METAL COMPLEXES, PRODUCTION AND USE THEREOF

PRIORITY CLAIM

This application claims the benefit of and priority to U.S. Ser. No. 62/357,033, filed Jun. 30, 2016 and is incorporated by reference in its entirety.

FIELD OF THE INVENTION

The invention relates to quinolinyldiamido transition metal complexes and intermediates and processes for use in making such quinolinyldiamido complexes. The transition metal complexes may be used as catalysts for alkene polymerization processes.

BACKGROUND OF THE INVENTION

Pyridyl amines have been used to prepare Group 4 complexes which are useful transition metal components in the polymerization of alkenes, see, for example, US 2002/0142912; U.S. Pat. No. 6,900,321; and U.S. Pat. No. 6,103,657; where the ligands have been used in complexes in which the ligands are coordinated in a bidentate fashion to the transition metal atom.

WO 2005/095469 shows catalyst compounds that use tridentate ligands through two nitrogen atoms (one amido and one pyridyl) and one oxygen atom.

US 2004/0220050A1 and WO 2007/067965 disclose complexes in which the ligand is coordinated in a tridentate fashion through two nitrogen (one amido and one pyridyl) and one carbon (aryl anion) donors.

A key step in the activation of these complexes is the insertion of an alkene into the metal-aryl bond of the catalyst precursor (Froese, R. D. J. et al., J. Am. Chem. Soc., 2007, 129, pp. 7831-7840) to form an active catalyst that has both a five-membered and a seven-membered chelate ring.

WO 2010/037059 discloses pyridine containing amines for use in pharmaceutical applications.

U.S. Pat. No. 8,158,733 describes catalyst compositions featuring 2-(2-aryloxy)-8-anilinoquinoline, 2,8-bis(2-aryloxy)quinoline, and 2,8-bis(2-aryloxy)dihydroquinoline ligands that do not feature a tridentate NNN donor ligand.

US 2012/0016092 describes catalyst compositions containing 2-imino-8-anilinoquinoline and 2-aminoalkyl-8-anilinoquinoline ligands having a one-atom linker between the quinoline and the nitrogen donor at the 2-position of the quinoline ring.

Organometallics, 2012, 31, p. 3241 by Hu et al. describes catalyst compositions containing 2-aminoalkyl-8-quinolinolato ligands that do not feature a tridentate NNN donor ligand.

Organometallics, 2013, 32, p. 2685 by Nifant'ev et al. describes catalyst compositions containing 2,8-bis(2-aryloxy)dihydroquinoline ligands that do not feature a tridentate NNN donor ligand.

Dalton Transactions, 2013, 42, p. 1501 by Nifant'ev et al. describes catalyst compositions containing 2-aryl-8-arylaminoquinoline ligands that do not feature a tridentate NNN donor ligand.

U.S. Pat. No. 7,858,718 describes catalyst compositions containing 2-aryl-8-anilinoquinoline ligands that do not feature a tridentate NNN donor ligand.

U.S. Pat. No. 7,973,116 describes catalyst compositions containing pyridyldiamide ligands, e.g., a pyridine-based ligand not a quinoline-based ligand.

There still is need for new catalyst compounds to widen the range of catalyst complexes available for superior performance in alkene polymerization. The performance may be varied with respect to the amount of polymer produced per amount of catalyst (generally referred to as the "activity") under the prevailing polymerization conditions; the molecular weight and molecular weight distribution achieved at a given temperature; and/or the placement of higher alpha-olefins in terms of the degree of stereoregular placement.

Further, there is a need in the art for new catalysts with high activity that can produce highly crystalline tactic (such as isotactic) propylene polymers.

SUMMARY OF THE INVENTION

This invention relates to novel transition metal complexes having tridentate NNN ligands. This invention also relates to quinolinyldiamido and related transition metal complexes represented by the formula (I) or (II):

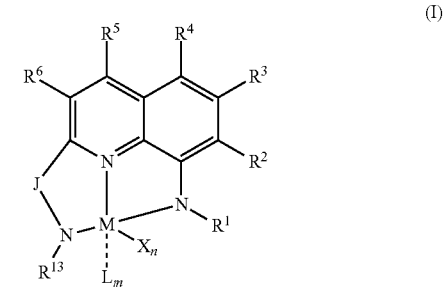

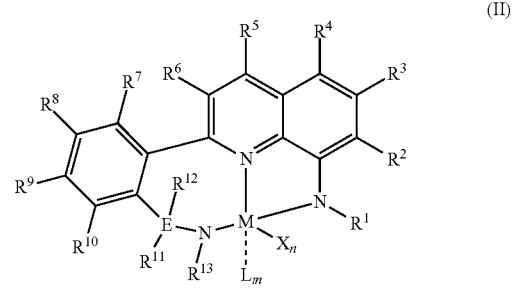

wherein:
M is a Group 3, 4, 5, 6, 7, 8, 9, 10, 11, or 12 metal;
J is a three-atom-length bridge between the quinoline and the amido nitrogen;
E is selected from carbon, silicon, or germanium;
X is an anionic leaving group;
L is a neutral Lewis base;
$R^1$ and $R^{13}$ are independently selected from the group consisting of hydrocarbyls, substituted hydrocarbyls, and silyl groups;
$R^2$ through $R^{12}$ are independently selected from the group consisting of hydrogen, hydrocarbyls, alkoxy, silyl, amino, aryloxy, substituted hydrocarbyls, halogen, and phosphino;
n is 1 or 2;
m is 0, 1, or 2
n+m is not greater than 4; and
any two adjacent R groups (e.g., $R^1$ & $R^2$, $R^2$ & $R^3$, etc.) may be joined to form a substituted or unsubstituted hydrocarbyl or heterocyclic ring, where the ring has 5, 6, 7, or 8 ring atoms and where substitutions on the ring can join to form additional rings;

any two X groups may be joined together to form a dianionic group;

any two L groups may be joined together to form a bidentate Lewis base; and an X group may be joined to an L group to form a monoanionic bidentate group.

This invention further relates to process to make the above complexes, process to make intermediates for the above complexes, and methods to polymerize olefins using the above complexes.

DETAILED DESCRIPTION

Figure 1:
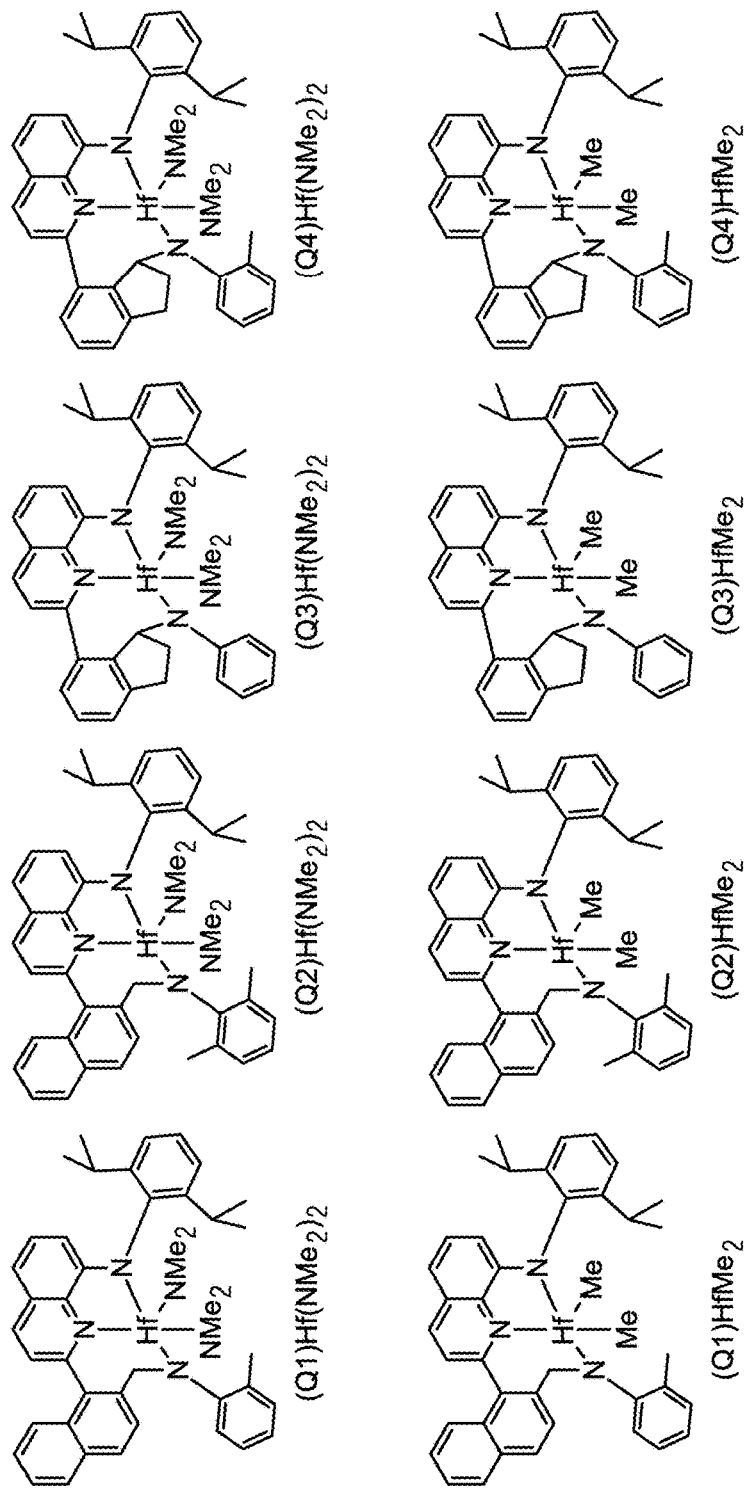
FIG. 1 shows line drawings of eight quinolinyldiamide complexes prepared in the Experimental section.

The specification describes transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which is believed to create a cation as a result of the removal of an anionic group, often referred to as a leaving group, from the transition metal.

As used herein, the numbering scheme for the Periodic Table groups is the new notation as set out in Chemical and Engineering News, 63(5), 27 (1985).

As used herein, Me is methyl, Et is ethyl, Bu is butyl, t-Bu and t-Bu are tertiary butyl, Pr is propyl, iPr and iPr are isopropyl, Cy is cyclohexyl, THF (also referred to as the is tetrahydrofuran, Bn is benzyl, and Ph is phenyl. Room temperature is 23° C., unless otherwise stated.

Unless otherwise indicated, the term "substituted" generally means that a hydrogen of the substituted species has been replaced with a different atom or group of atoms. For example, methyl-cyclopentadiene is cyclopentadiene that has been substituted with a methyl group. Likewise, picric acid can be described as phenol that has been substituted with three nitro groups, or, alternatively, as benzene that has been substituted with one hydroxy and three nitro groups.

The terms "hydrocarbyl radical," "hydrocarbyl," and "hydrocarbyl group" are used interchangeably throughout this document. Likewise, the terms "group," "radical," and "substituent" are also used interchangeably in this document. For purposes of this disclosure, "hydrocarbyl radical" is defined to be $C_1$-$C_{100}$ radicals, that may be linear, branched, or cyclic, and when cyclic, aromatic or non-aromatic.

A substituted hydrocarbyl radical is a hydrocarbyl radical in which at least one hydrogen atom of the hydrocarbyl radical has been substituted with at least one functional group such as F, Cl, Br, I, $C(O)R^*$, $C(O)NR^*_2$, $C(O)OR^*$, $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$, and the like (where $R^*$ is independently a hydrogen or hydrocarbyl radical, and two or more $R^*$ may join together to form a substituted or unsubstituted saturated, partially unsaturated or aromatic cyclic or polycyclic ring structure), or where at least one heteroatom has been inserted within a hydrocarbyl ring.

The term "catalyst system" is defined to mean a complex/activator pair. When "catalyst system" is used to describe such a pair before activation, it means the unactivated catalyst complex (precatalyst) together with an activator and, optionally, a co-activator. When it is used to describe such a pair after activation, it means the activated complex and the activator or other charge-balancing moiety. The transition metal compound may be neutral as in a precatalyst, or a charged species with a counter ion as in an activated catalyst system.

The term "complex," may also be referred to as catalyst precursor, precatalyst, catalyst, catalyst compound, transition metal compound, or transition metal complex. These words are used interchangeably. Activator and cocatalyst are also used interchangeably.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments, a co-activator can be pre-mixed with the transition metal compound to form an alkylated transition metal compound.

For purposes herein, an "olefin," alternatively referred to as "alkene," is a linear, branched, or cyclic compound comprising carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have a "propylene" content of 35 wt % to 55 wt %, it is understood that the mer unit in the copolymer is derived from propylene in the polymerization reaction and said derived units are present at 35 wt % to 55 wt %, based upon the weight of the copolymer. A higher α-olefin is defined to be an α-olefin having 4 or more carbon atoms. For the purposes of this disclosure, ethylene is considered an alpha-olefin.

For purposes herein, a "polymer" has two or more of the same or different "mer" units. A "homopolymer" is a polymer having mer units that are the same. A "copolymer" is a polymer having two or more mer units that are different from each other. A "terpolymer" is a polymer having three mer units that are different from each other. "Different" in reference to mer units indicates that the mer units differ from each other by at least one atom or are different isomerically. Accordingly, the definition of copolymer, as used herein, includes terpolymers and the like. An "ethylene polymer" or "ethylene copolymer" is a polymer or copolymer comprising at least 50 mol % ethylene derived units, a "propylene polymer" or "propylene copolymer" is a polymer or copolymer comprising at least 50 mol % propylene derived units, and so on.

As used herein, Mn is number average molecular weight, Mw is weight average molecular weight, and Mz is z average molecular weight, wt % is weight percent, and mol % is mole percent. Molecular weight distribution (MWD), also referred to as polydispersity index (PDI), is defined to be Mw divided by Mn. Unless otherwise noted, all molecular weight units (e.g., Mw, Mn, Mz) are reported in g/mol.

Unless otherwise noted all melting points ($T_m$) are DSC second melt.

A "ring carbon atom" is a carbon atom that is part of a cyclic ring structure. By this definition, a benzyl group has six ring carbon atoms and para-methylstyrene also has six ring carbon atoms.

The term "aryl" or "aryl group" means a six carbon aromatic ring and the substituted variants thereof, including but not limited to, phenyl, 2-methyl-phenyl, xylyl, 4-bromo-xylyl. Likewise heteroaryl means an aryl group where a ring carbon atom (or two or three ring carbon atoms) has been replaced with a heteroatom, preferably N, O, or S.

The term "ring atom" means an atom that is part of a cyclic ring structure. By this definition, a benzyl group has six ring atoms and tetrahydrofuran has five ring atoms.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom substituted ring. A substituted heterocyclic ring is a heterocyclic ring in which at least one hydrogen atom of the heterocyclic ring has been substituted with a hydrocarbyl group, a substituted hydrocarbyl group or a functional group such as F, Cl, Br, I, C(O)R*, C(O)NR*$_2$, C(O)OR*, NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$, and the like (where R* is independently a hydrogen or hydrocarbyl radical, and two or more R* may join together to form a substituted or unsubstituted saturated, partially unsaturated or aromatic cyclic or polycyclic ring structure).

As used herein the term "aromatic" also refers to pseudoaromatic heterocycles which are heterocyclic substituents that have similar properties and structures (nearly planar) to aromatic heterocyclic ligands, but are not by definition aromatic; likewise, the term aromatic also refers to substituted aromatics.

Catalyst Compounds

This invention relates to quinolinyldiamido transition metal complexes where a three-atom linker is used between the quinoline and the nitrogen donor in the 2-position of the quinoline ring. The has been found to be an important aspect because the use of the three-atom linker is believed to yield a metal complex with a seven-membered chelate ring that is not coplanar with the other five-membered chelate ring. The resulting complex is thought to be effectively chiral ($C_1$ symmetry), even when there are no permanent stereocenters present. This is a desirable catalyst feature, for example, for the production of isotactic polyolefins.

This invention further relates to a quinolinyldiamido transition metal complex represented by Formula (I), preferably by Formula (II), preferably by Formula (III):

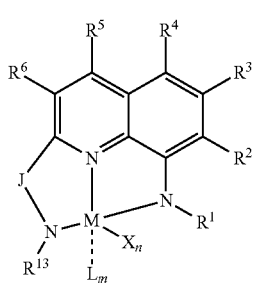

(I)

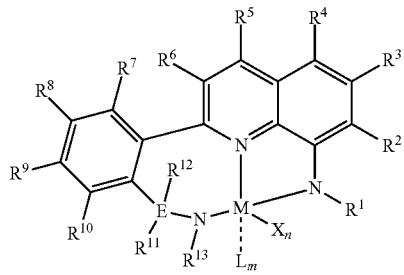

(II)

The complex of claim 1, wherein the complex is further represented by Formula:

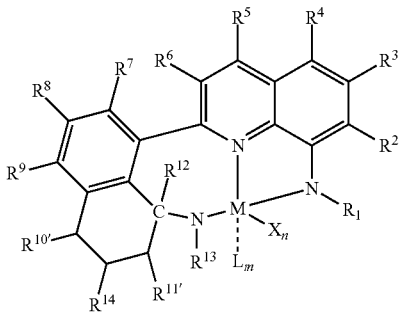

(III)

wherein:

M is a Group 3, 4, 5, 6, 7, 8, 9, 10, 11, or 12 metal (preferably a group 4 metal);

J is group comprising a three-atom-length bridge between the quinoline and the amido nitrogen, preferably a group containing up to 50 non-hydrogen atoms;

E is carbon, silicon, or germanium;

X is an anionic leaving group, (such as a hydrocarbyl group or a halogen);

L is a neutral Lewis base;

$R^1$ and $R^{13}$ are independently selected from the group consisting of hydrocarbyls, substituted hydrocarbyls, and silyl groups;

$R^2$, $R^3$, $R^4$, $R^5$, $R^6$, $R^7$, $R^8$, $R^9$, $R^{10}$, $R^{10'}$, $R^{11}$, $R^{11'}$, $R^{12}$, and $R^{14}$ are independently hydrogen, hydrocarbyl, alkoxy, silyl, amino, aryloxy, substituted hydrocarbyl, halogen, or phosphino;

n is 1 or 2;

m is 0, 1, or 2, where n+m is not greater than 4; and any two R groups (e.g., $R^1$ & $R^2$, $R^2$ & $R^3$, $R^{10}$ and $R^{11}$, etc.) may be joined to form a substituted hydrocarbyl, unsubstituted hydrocarbyl, substituted heterocyclic, or unsubstituted heterocyclic, saturated or unsaturated ring, where the ring has 5, 6, 7, or 8 ring atoms and where substitutions on the ring can join to form additional rings;

any two X groups may be joined together to form a dianionic group;

any two L groups may be joined together to form a bidentate Lewis base; and any X group may be joined to an L group to form a monoanionic bidentate group.

Preferably, M is a Group 4 metal, such as zirconium or hafnium.

In a preferred embodiment, J is an aromatic substituted or unsubstituted hydrocarbyl (preferably a hydrocarbyl) having from 3 to 30 non-hydrogen atoms, preferably J is represented by the formula:

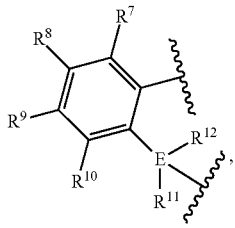

more preferably J is

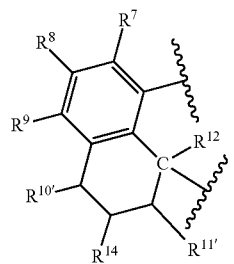

where $R^7$, $R^8$, $R^9$, $R^{10}$, $R^{10'}$, $R^{11}$, $R^{11'}$, $R^{12}$, $R^{14}$ and E are as defined above, and any two R groups (e.g., $R^7$ & $R^8$, $R^8$ & $R^9$, $R^9$ & $R^{10}$, $R^{10}$ & $R^{11}$, etc.) may be joined to form a substituted or unsubstituted hydrocarbyl or heterocyclic ring, where the ring has 5, 6, 7, or 8 ring atoms (preferably 5 or 6 atoms), and said ring may be saturated or unsaturated (such as partially unsaturated or aromatic), preferably J is an arylalkyl (such as arylmethyl, etc.) or dihydro-1H-indenyl, or tetrahydronaphthalenyl group.

In embodiments of the invention, J is selected from the following structures:

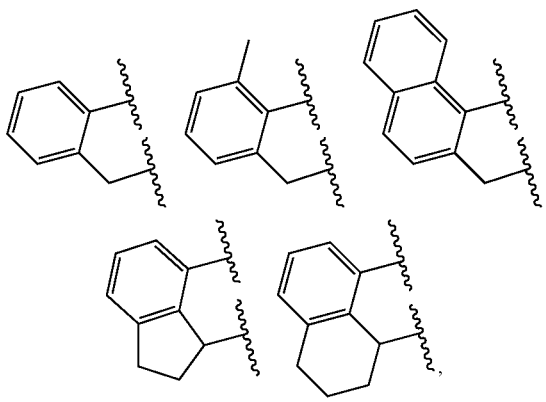

where ⌇ indicates connection to the complex.

In embodiments of the invention, E is carbon.

In embodiments of the invention, X is alkyl (such as alkyl groups having 1 to 10 carbons, such as methyl, ethyl, propyl, butyl, pentyl, hexyl, heptyl, octyl, nonyl, decyl, and isomers thereof), aryl, hydride, alkylsilane, fluoride, chloride, bromide, iodide, triflate, carboxylate, amido (such as $NMe_2$), or alkylsulfonate.

In embodiments of the invention, L is an ether, amine or thioether.

In embodiments of the invention, $R^7$ and $R^8$ are joined to form a six-membered aromatic ring with the joined $R^7R^8$ group being —CH=CHCH=CH—.

In embodiments of the invention, $R^{10}$ and $R^{11}$ are joined to form a five-membered ring with the joined $R^{10}R^{11}$ group being —$CH_2CH_2$—.

In embodiments of the invention, $R^{10}$ and $R^{11}$ are joined to form a six-membered ring with the joined $R^{10}R^{11}$ group being —$CH_2CH_2CH_2$—.

In embodiments of the invention, $R^1$ and $R^{13}$ may be independently selected from phenyl groups that are variously substituted with between zero to five substituents that include F, Cl, Br, I, $CF_3$, $NO_2$, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof.

In a preferred embodiment of the invention, the quinolinyldiamido transition metal complex represented by the Formula II above where:

M is a Group 4 metal (preferably hafnium);
E is selected from carbon, silicon, or germanium (preferably carbon);
X is an alkyl, aryl, hydride, alkylsilane, fluoride, chloride, bromide, iodide, triflate, carboxylate, amido, alkoxo, or alkylsulfonate;
L is an ether, amine, or thioether;
$R^1$ and $R^{13}$ are independently selected from the group consisting of hydrocarbyls, substituted hydrocarbyls, and silyl groups (preferably aryl);
$R^2$, $R^3$, $R^4$, $R^5$, $R^6$, $R^7$, $R^8$, $R^9$, $R^{10}$, $R^{11}$, and $R^{12}$ are independently hydrogen, hydrocarbyl, alkoxy, silyl, amino, aryloxy, substituted hydrocarbyls, halogen, and phosphino;
n is 1 or 2;
m is 0, 1, or 2;
n+m is from 1 to 4; and
two X groups may be joined together to form a dianionic group;
two L groups may be joined together to form a bidentate Lewis base;
an X group may be joined to an L group to form a monoanionic bidentate group;
$R^7$ and $R^8$ may be joined to form a ring (preferably an aromatic ring, a six-membered aromatic ring with the joined $R^7R^8$ group being —CH=CHCH=CH—);
$R^{10}$ and $R^{11}$ may be joined to form a ring (preferably a five-membered ring with the joined $R^{10}R^{11}$ group being —$CH_2CH_2$—, a six-membered ring with the joined $R^{10}R^{11}$ group being —$CH_2CH_2CH_2$—).

In embodiments of Formula I, II, and III, $R^4$, $R^5$, and $R^6$ are independently selected from the group consisting of hydrogen, hydrocarbyls, substituted hydrocarbyls, alkoxy, aryloxy, halogen, amino, and silyl, and wherein adjacent R groups ($R^4$ and $R^5$ and/or $R^5$ and $R^6$) may be joined to form a substituted hydrocarbyl, unsubstituted hydrocarbyl, unsubstituted heterocyclic ring or substituted heterocyclic ring, where the ring has 5, 6, 7, or 8 ring atoms and where substitutions on the ring can join to form additional rings.

In embodiments of Formula I, II, and III, $R^7$, $R^8$, $R^9$, and $R^{10}$ are independently selected from the group consisting of hydrogen, hydrocarbyls, substituted hydrocarbyls, alkoxy, halogen, amino, and silyl, and wherein adjacent R groups ($R^7$ and $R^8$ and/or $R^9$ and $R^{10}$) may be joined to form a saturated, substituted hydrocarbyl, unsubstituted hydrocarbyl, unsubstituted heterocyclic ring or substituted heterocyclic ring, where the ring has 5, 6, 7, or 8 ring carbon atoms and where substitutions on the ring can join to form additional rings.

In embodiments of Formula I, II, and III, $R^2$ and $R^3$ are each, independently, selected from the group consisting of hydrogen, hydrocarbyls, and substituted hydrocarbyls, alkoxy, silyl, amino, aryloxy, halogen, and phosphino, $R^2$ and $R^3$ may be joined to form a saturated, substituted or unsubstituted hydrocarbyl ring, where the ring has 4, 5, 6, or 7 ring carbon atoms and where substitutions on the ring can join to form additional rings, or $R^2$ and $R^3$ may be joined to form a saturated heterocyclic ring, or a saturated substituted heterocyclic ring where substitutions on the ring can join to form additional rings.

In embodiments of Formula I, II, and III, $R^{11}$ and $R^{12}$ are each, independently, selected from the group consisting of hydrogen, hydrocarbyls, and substituted hydrocarbyls, alkoxy, silyl, amino, aryloxy, halogen, and phosphino, $R^{11}$ and $R^{12}$ may be joined to form a saturated, substituted or unsubstituted hydrocarbyl ring, where the ring has 4, 5, 6, or 7 ring carbon atoms and where substitutions on the ring can join to form additional rings, or $R^{11}$ and $R^{12}$ may be joined to form a saturated heterocyclic ring, or a saturated substituted heterocyclic ring where substitutions on the ring can join to form additional rings, or $R^{11}$ and $R^{10}$ may be joined to form a saturated heterocyclic ring, or a saturated substituted heterocyclic ring where substitutions on the ring can join to form additional rings.

In embodiments of Formula I, II, or III, $R^1$ and $R^{13}$ may be independently selected from phenyl groups that are variously substituted with between zero to five substituents that include F, Cl, Br, I, $CF_3$, $NO_2$, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof.

In embodiments of Formula II, preferred $R^{12}$-E-$R^{11}$ groups include $CH_2$, $CMe_2$, $SiMe_2$, $SiEt_2$, $SiPr_2$, $SiBu_2$, $SiPh_2$, $Si(aryl)_2$, $Si(alkyl)_2$, CH(aryl), CH(Ph), CH(alkyl), and CH(2-isopropylphenyl), where alkyl is a $C_1$ to $C_{40}$ alkyl group (preferably $C_1$ to $C_{20}$ alkyl, preferably one or more of methyl, ethyl, propyl, butyl, pentyl, hexyl, heptyl, octyl, nonyl, decyl, undecyl, dodecyl, and isomers thereof), aryl is a $C_5$ to $C_{40}$ aryl group (preferably a $C_6$ to $C_{20}$ aryl group, preferably phenyl or substituted phenyl, preferably phenyl, 2-isopropylphenyl, or 2-tertbutylphenyl).

In embodiments of Formula III, $R^{11}$, $R^{12}$, $R^9$, $R^{14}$, and $R^{10}$ are independently selected from the group consisting of hydrogen, hydrocarbyls, substituted hydrocarbyls, alkoxy, halogen, amino, and silyl, and wherein adjacent R groups ($R^{10}$ and $R^{14}$, and/or $R^{11}$ and $R^{14}$, and/or $R^9$ and $R^{10}$) may be joined to form a saturated, substituted hydrocarbyl, unsubstituted hydrocarbyl, unsubstituted heterocyclic ring or substituted heterocyclic ring, where the ring has 5, 6, 7, or 8 ring carbon atoms and where substitutions on the ring can join to form additional rings.

Preferably, the R groups above (i.e., any of $R^2$ to $R^{14}$) and other R groups mentioned hereafter, contain from 1 to 30, preferably 2 to 20 carbon atoms, especially from 6 to 20 carbon atoms. Preferably, the R groups above (i.e., any of $R^2$ to $R^{14}$) and other R groups mentioned hereafter, are independently selected from the group consisting of hydrogen, methyl, ethyl, phenyl, isopropyl, isobutyl, trimethylsilyl, and —$CH_2$—$Si(Me)_3$.

In one potential embodiment the quinolinyldiamide complex is linked to one or more additional transition metal complex, such as a quinolinyldiamide complex or a metallocene, through an R group in such a fashion as to make a bimetallic, trimetallic, or multimetallic complex that may be used as a catalyst component for olefin polymerization. The linker R– group in such a complex preferably contains 1 to 30 carbon atoms.

Preferably, M is Ti, Zr, or Hf, and E is carbon, with Zr or Hf based complexes being especially preferred.

In any embodiment described herein, E is carbon and $R^{12}$ and $R^{11}$ are independently selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyl groups with from one to ten carbons.

In any embodiment described herein of Formula II or III, $R^{11}$ and $R^{12}$ are independently selected from hydrogen, methyl, ethyl, phenyl, isopropyl, isobutyl, —$CH_2$—$Si(Me)_3$, and trimethylsilyl.

In any embodiment described herein of Formula II or III, $R^7$, $R^8$, $R^9$, and $R^{10}$ are independently selected from hydrogen, methyl, ethyl, propyl, isopropyl, phenyl, cyclohexyl, fluoro, chloro, methoxy, ethoxy, phenoxy, —$CH_2$—$Si(Me)_3$, and trimethylsilyl.

In any embodiment described herein of Formula I, II, or III, $R^2$, $R^3$, $R^4$, $R^5$, and $R^6$ are independently selected from the group consisting of hydrogen, hydrocarbyls, alkoxy, silyl, amino, substituted hydrocarbyls, and halogen.

In any embodiment described herein of Formula III, $R^{10}$, $R^{11}$ and $R^{14}$ are independently selected from hydrogen, methyl, ethyl, phenyl, isopropyl, isobutyl, —$CH_2$—$Si(Me)_3$, and trimethylsilyl.

In any embodiment described herein of Formula I, II, or III, each L is independently selected from $Et_2O$, MeOtBu, $Et_3N$, $PhNMe_2$, $MePh_2N$, tetrahydrofuran, and dimethylsulfide.

In any embodiment described herein of Formula I, II, or III, each X is independently selected from methyl, benzyl, trimethylsilyl, neopentyl, ethyl, propyl, butyl, phenyl, hydrido, chloro, fluoro, bromo, iodo, dimethylamido, diethylamido, dipropylamido, and diisopropylamido.

In any embodiment described herein of Formula I, II, or III, IV is 2,6-diisopropylphenyl, 2,4,6-triisopropylphenyl, 2,6-diisopropyl-4-methylphenyl, 2,6-diethylphenyl, 2-ethyl-6-isopropylphenyl, 2,6-bis(3-pentyl)phenyl, 2,6-dicyclopentylphenyl, or 2,6-dicyclohexylphenyl.

In any embodiment described herein of Formula I, II, or III, $R^{13}$ is phenyl, 2-methylphenyl, 2-ethylphenyl, 2-propylphenyl, 2,6-dimethylphenyl, 2-isopropylphenyl, 4-methylphenyl, 3,5-dimethylphenyl, 3,5-di-tert-butylphenyl, 4-fluorophenyl, 3-methylphenyl, 4-dimethylaminophenyl, or 2-phenylphenyl.

In any embodiment described herein of Formula II, J is dihydro-1H-indenyl and $R^1$ is 2,6-dialkylphenyl or 2,4,6-trialkylphenyl.

In any embodiment described herein of Formula I, II, or III, $R^1$ is 2,6-diisopropylphenyl and $R^{13}$ is a hydrocarbyl group containing 1, 2, 3, 4, 5, 6, or 7 carbon atoms.

In another aspect of the invention there are provided various processes for synthesizing the complexes described herein.

Ligand Synthesis

The quinolinyldiamine ligands described herein are generally prepared in multiple steps. The main step in the synthesis of the quinolinyldiamine ligand is the carbon-carbon bond coupling step shown below in Scheme 1, wherein fragment 1 and fragment 2 are joined together in a transition metal mediated reaction. In the specific examples described herein the coupling step involves the use of $Pd(PPh_3)_4$, but other transition metal catalysts (e.g., Ni or Cu containing complexes) are also useful for this type of coupling reaction. In the specific examples described herein, the W* and Y* groups used were a boronic acid ester and a halide, respectively. This choice was suitable for the Pd-mediated coupling step, but other groups may also be useful for the coupling reaction. Other possible W* and Y* groups of interest include alkali metal (e.g., Li), alkaline earth metal halide (e.g., MgBr), zinc halide (e.g., ZnCl), zincate, halide, and triflate. In Scheme 1, $R^1$ through $R^{13}$ and E are as described above.

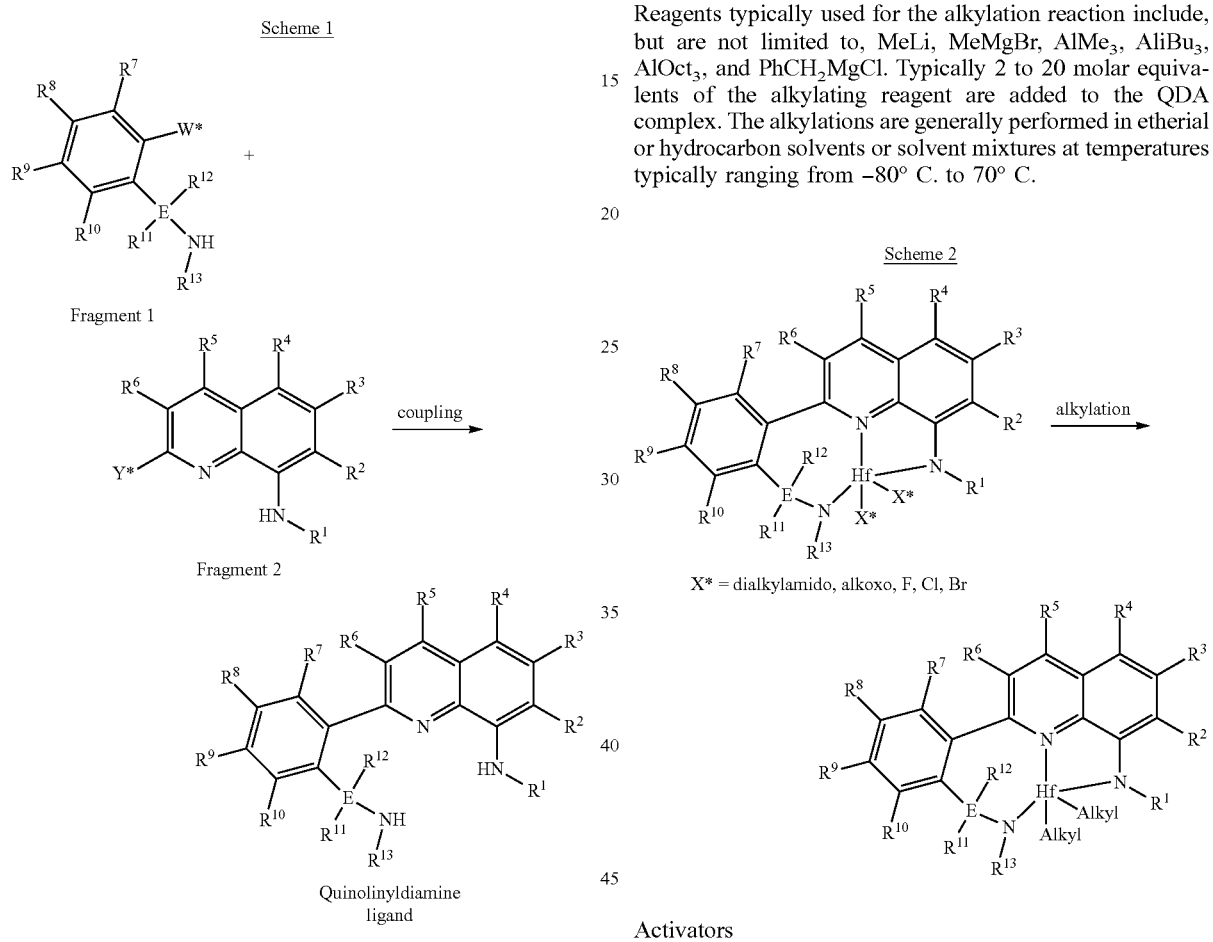

One method for the preparation of transition metal quinolinyldiamide complexes is by reaction of the quinolinyldiamine ligand with a metal reactant containing anionic basic leaving groups. Typical anionic basic leaving groups include dialkylamido, benzyl, phenyl, hydrido, and methyl. In this reaction, the role of the basic leaving group is to deprotonate the quinolinyldiamine ligand. Suitable metal reactants for this type of reaction include, but are not limited to, $HfBn_4$ ($Bn=CH_2Ph$), $ZrBn_4$, $TiBn_4$, $ZrBn_2Cl_2(OEt_2)$, $HfBn_2Cl_2(OEt_2)_2$, $Zr(NMe_2)_2Cl_2$(dimethoxyethane), $Hf(NMe_2)_2Cl_2$(dimethoxyethane), $Hf(NMe_2)_4$, $Zr(NMe_2)_4$, and $Hf(NEt_2)_4$. In the specific examples presented herein $Hf(NMe_2)_4$ is reacted with a quinolinyldiamine ligand at elevated temperatures to form the quinolinyldiamide complex with the formation of two molar equivalents of dimethylamine, which is lost or removed before the quinolinyldiamide complex is isolated.

A second method for the preparation of transition metal quinolinyldiamide complexes is by reaction of the quinolinyldiamine ligand with an alkali metal or alkaline earth metal base (e.g., BuLi, EtMgBr) to deprotonate the ligand, followed by reaction with a metal halide (e.g., $HfCl_4$, $ZrCl_4$).

Quinolinyldiamide (QDA) metal complexes that contain metal-halide, alkoxide, or amido leaving groups may be alkylated by reaction with organolithium, Grignard, and organoaluminum reagents as shown in Scheme 2. In the alkylation reaction the alkyl groups are transferred to the QDA metal center and the leaving groups are removed. In Scheme 2, $R^1$ through $R^{13}$ and E are as described above and X* is a halide, alkoxide, or dialkylamido leaving group. Reagents typically used for the alkylation reaction include, but are not limited to, MeLi, MeMgBr, $AlMe_3$, $AliBu_3$, $AlOct_3$, and $PhCH_2MgCl$. Typically 2 to 20 molar equivalents of the alkylating reagent are added to the QDA complex. The alkylations are generally performed in etherial or hydrocarbon solvents or solvent mixtures at temperatures typically ranging from −80° C. to 70° C.

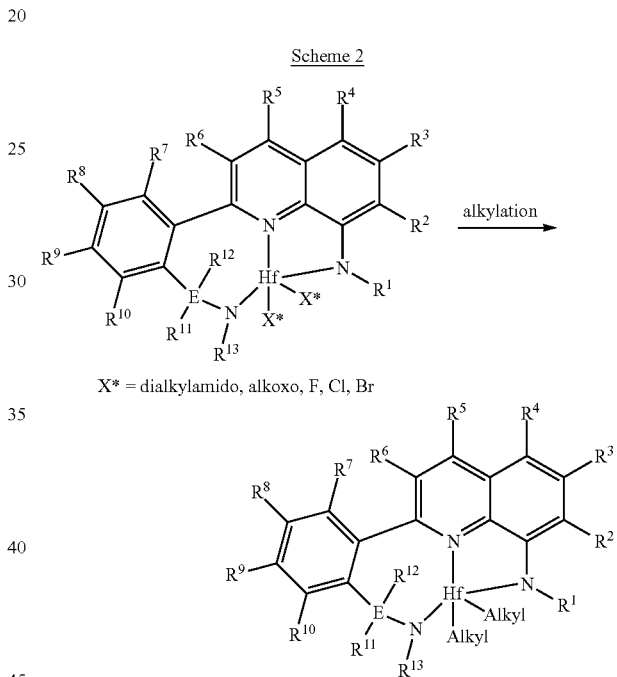

Activators

After the complexes have been synthesized, catalyst systems may be formed by combining the complexes with activators in any manner known from the literature including by supporting them for use in slurry or gas phase polymerization. The catalyst systems may also be added to or generated in solution polymerization or bulk polymerization (in the monomer). The catalyst system typically comprises a complex as described above and an activator such as alumoxane or a non-coordinating anion. Activation may be performed using alumoxane solution including methyl alumoxane, referred to as MAO, as well as modified MAO, referred to herein as MMAO, containing some higher alkyl groups to improve the solubility. Particularly useful MAO can be purchased from Albemarle in a 10 wt % solution in toluene. The catalyst system employed in the present invention preferably uses an activator selected from alumoxanes, such as methyl alumoxane, modified methyl alumoxane, ethyl alumoxane, iso-butyl alumoxane, and the like. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

When an alumoxane or modified alumoxane is used, the catalyst complex-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-complex ratio is 1:1 molar ratio.

Activation may also be performed using non-coordinating anions, referred to as NCA's, of the type described in EP 277 003 A1 and EP 277 004 A1. NCA may be added in the form of an ion pair using, for example, [DMAH]$^+$ [NCA]$^-$ in which the N,N-dimethylanilinium (DMAH) cation reacts with a basic leaving group on the transition metal complex to form a transition metal complex cation and [NCA]$^-$. The cation in the precursor may, alternatively, be trityl. Alternatively, the transition metal complex may be reacted with a neutral NCA precursor, such as $B(C_6F_5)_3$, which abstracts an anionic group from the complex to form an activated species. Useful activators include N,N-dimethylanilinium tetrakis(pentafluorophenyl)borate (i.e., [PhNMe$_2$H][B(C$_6$F$_5$)$_4$]) and N,N-dimethylanilinium tetrakis(heptafluoronaphthyl) borate, where Ph is phenyl, and Me is methyl.

Non-coordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. The term non-coordinating anion includes ionic activators and Lewis acid activators.

Additionally, preferred activators useful herein include those described in U.S. Pat. No. 7,247,687 at column 169, line 50 to column 174, line 43, particularly column 172, line 24 to column 173, line 53.

Illustrative, but not limiting examples of boron compounds which may be used as an activating cocatalyst are the compounds described as (and particularly those specifically listed as) activators in U.S. Pat. No. 8,658,556 and or U.S. Pat. No. 6,211,105, which are incorporated by reference herein.

Preferably, the NCA containing activator is one or more of N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis (perfluorophenyl)borate, methyl bis(hydrogenated tallow) ammonium tetrakis(perfluorophenyl)borate, or methyl dialkylammonium tetrakis(perfluoroaryl)borate.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(perfluorophenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph$_3$C$^+$][B(C$_6$F$_5$)$_4^-$], [Me$_3$NH$^+$][B(C$_6$F$_5$)$_4^-$]; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium) tetrakis(pentafluorophenyl)borate, trialkylammonium tetrakis-(2,3,4,6-tetrafluorophenyl) borate, N,N-dialkylanilinium tetrakis-(2,3,4,6-tetrafluorophenyl)borate, trialkylammonium tetrakis (perfluoronaphthyl)borate, N,N-dialkylanilinium tetrakis (perfluoronaphthyl)borate, trialkylammonium tetrakis (perfluorobiphenyl)borate, N,N-dialkylanilinium tetrakis (perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl)phenyl)borate, di-(i-propyl)ammonium tetrakis(pentafluorophenyl)borate, (where alkyl is methyl, ethyl, propyl, n-butyl, sec-butyl, or t-butyl).

When an NCA (such as an ionic or neutral stoichiometric activator) is used, the catalyst complex-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2.

Alternately, a co-activator may also be used in the catalyst system herein. The complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Supports

In some embodiments, the complexes described herein may be supported (with or without an activator) by any method effective to support other coordination catalyst systems, effective meaning that the catalyst so prepared can be used for oligomerizing or polymerizing olefin in a heterogeneous process. The catalyst precursor, activator, co-activator if needed, suitable solvent, and support may be added in any order or simultaneously. Typically, the complex and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The complex may also be supported absent the activator; in that case, the activator (and co-activator if needed) is added to a polymerization process's liquid phase. Additionally, two or more different complexes may be placed on the same support. Likewise, two or more activators or an activator and co-activator may be placed on the same support.

Suitable solid particle supports are typically comprised of polymeric or refractory oxide materials, each being preferably porous. Preferably any support material that has an average particle size greater than 10 µm is suitable for use in this invention. Various embodiments select a porous support material, such as for example, talc, inorganic oxides, inorganic chlorides, for example, magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component, however, an additional activator may also be used.

The support material may be pretreated by any number of methods. For example, inorganic oxides may be calcined, chemically treated with dehydroxylating agents, such as, aluminum alkyls and the like, or both.

As stated above, polymeric carriers will also be suitable in accordance with the invention, see, for example, the descriptions in WO 95/15815 and U.S. Pat. No. 5,427,991. The methods disclosed may be used with the catalyst complexes, activators, or catalyst systems of this invention to adsorb or absorb them on the polymeric supports, particularly if made up of porous particles, or may be chemically bound through functional groups bound to or in the polymer chains.

Useful supports typically have a surface area of from 10-700 $m^2/g$, a pore volume of 0.1-4.0 cc/g and an average particle size of 10-500 µm. Some embodiments select a surface area of 50-500 $m^2/g$, a pore volume of 0.5-3.5 cc/g, or an average particle size of 20-200 µm. Other embodiments select a surface area of 100-400 $m^2/g$, a pore volume of 0.8-3.0 cc/g, and an average particle size of 30-100 µm. Useful supports typically have a pore size of 10-1000 Angstroms, alternatively 50-500 Angstroms, or 75-350 Angstroms.

The catalyst complexes described herein are generally deposited on the support at a loading level of 10-100 micromoles of complex per gram of solid support; alternately 20-80 micromoles of complex per gram of solid support; or 40-60 micromoles of complex per gram of support. But greater or lesser values may be used provided that the total amount of solid complex does not exceed the support's pore volume.

Polymerization

For purposes of this invention and the claims thereto, the term "continuous process" means a system that operates without interruption or cessation. For example, a continuous process to produce a polymer would be one where the reactants are continually introduced into one or more reactors and polymer product is continually withdrawn.

For purposes of this invention and the claims thereto, a solution polymerization means a polymerization process in which the polymer produced is dissolved in a liquid polymerization medium at polymerization condition, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva, and J. C. Pinto, Ind. Eng, Chem. Res., 29, 2000, p. 4627.

For purposes of this invention and the claims thereto, a bulk polymerization means a polymerization process in which the monomers and/or comonomers being polymerized are used as a solvent or diluent using little or no inert solvent as a solvent or diluent. A small faction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

"Catalyst activity" is a measure of how many grams of polymer (P) are produced using a polymerization catalyst comprising W mmol of transition metal (M), over a period of time of T hours; and may be expressed by the following formula: $P/(T \times W)$.

The inventive catalyst complexes described herein are useful in polymerizing unsaturated monomers conventionally known to undergo coordination catalyst-catalyzed polymerization such as solution, slurry, gas-phase, and high-pressure polymerization. Typically, one or more of the complexes described herein, one or more activators, and one or more monomers are contacted to produce polymer. In certain embodiments, the complexes may be supported and, as such, will be particularly useful in the known, fixed-bed, moving-bed, fluid-bed, slurry, solution, or bulk operating modes conducted in single, series, or parallel reactors.

One or more reactors in series or in parallel may be used in the present invention. The complexes, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the complex is activated in the reactor in the presence of olefin.

In a particularly preferred embodiment, the polymerization process is a continuous process.

Polymerization processes used herein typically comprise contacting one or more alkene monomers with the complexes (and, optionally, activator) described herein. For purpose of this invention alkenes are defined to include multi-alkenes (such as dialkenes) and alkenes having just one double bond. Polymerization may be homogeneous (solution or bulk polymerization) or heterogeneous (slurry—in a liquid diluent, or gas phase—in a gaseous diluent). In the case of heterogeneous slurry or gas phase polymerization, the complex and activator may be supported. Silica is useful as a support herein. Hydrogen may be used in the practice of this invention.

The present polymerization processes may be conducted under conditions preferably including a temperature of about 30° C. to about 200° C., preferably from 60° C. to 195° C., preferably from 75° C. to 190° C., preferably from 80° C. to 130° C., preferably 85° C. to 105° C.

The present polymerization processes may be conducted at a pressure of from 0.05 MPa to 1500 MPa. In a preferred embodiment, the pressure is between 1.7 MPa and 30 MPa, or in another embodiment, especially under supercritical conditions, the pressure is between 15 MPa and 1500 MPa.

Monomers

Monomers useful herein include olefins having from 2 to 20 carbon atoms, alternately 2 to 12 carbon atoms (preferably ethylene, propylene, butylene, pentene, hexene, heptene, octene, nonene, decene, and dodecene) and optionally also polyenes (such as dienes). Particularly preferred monomers include ethylene, and mixtures of $C_2$ to $C_{10}$ alpha olefins, such as ethylene-propylene, ethylene-hexene, ethylene-octene, propylene-hexene, and the like.

The complexes described herein are also particularly effective for the polymerization of ethylene, either alone or in combination with at least one other olefinically unsaturated monomer, such as a $C_3$ to $C_{20}$ α-olefin, and particularly a $C_3$ to $C_{12}$ α-olefin. Likewise, the present complexes are also particularly effective for the polymerization of propylene, either alone or in combination with at least one other olefinic ally unsaturated monomer, such as ethylene or a $C_4$ to $C_{20}$ α-olefin, and particularly a $C_4$ to $C_{20}$ α-olefin. Examples of preferred α-olefins include ethylene, propylene, butene-1, pentene-1, hexene-1, heptene-1, octene-1, nonene-1, decene-1, dodecene-1, 4-methylpentene-1, 3-methylpentene-1,3,5,5-trimethylhexene-1, and 5-ethylnonene-1.

In some embodiments, the monomer mixture may also comprise one or more dienes at up to 10 wt %, such as from 0.00001 to 1.0 wt %, for example, from 0.002 to 0.5 wt %, such as from 0.003 to 0.2 wt %, based upon the monomer mixture. Non-limiting examples of useful dienes include, cyclopentadiene, norbornadiene, dicyclopentadiene, 5-ethylidene-2-norbornene, 5-vinyl-2-norbornene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,9-dimethyl-1,9-decadiene.

The polymerization of propylene or propylene-rich copolymers with ethylene is expected to produce polymer with crystalline isotactic polypropylene runs. This is expected because the catalyst family has a seven-membered chelate ring, which effectively makes the catalyst $C_1$ symmetric (i.e., no symmetry) in use.

Scavengers

In some embodiments, when using the complexes described herein, particularly when they are immobilized on a support, the catalyst system will additionally comprise one or more scavenging compounds. Here, the term scavenging compound means a compound that removes polar impurities from the reaction environment. These impurities adversely affect catalyst activity and stability. Typically, the scavenging compound will be an organometallic compound such as the Group-13 organometallic compounds of U.S. Pat. No. 5,153,157; U.S. Pat. No. 5,241,025; WO-A-91/09882; WO-A-94/03506; WO-A-93/14132; and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes (methylalumoxane), aluminum oxides (e.g., bis(di-isobutylaluminum)oxide), and modified alumoxanes (e.g., MMAO-3A) also may be added in scavenging quantities with other activators such as $[Me_2HNPh]^+[B(pfp)_4]^-$ or $B(pfp)_3$ (perfluorophenyl=pfp=$C_6F_5$).

Polymer Products

While the molecular weight of the polymers produced herein can be influenced by reactor conditions including temperature, monomer concentration and pressure, the presence of chain-terminating or chain-transfer agents and the like, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC (as described below).

The polymers produced herein may have a melt flow rate (MFR) of at least 0.01 dg/min (preferably 0.1 to 50 dg/min, preferably 0.2 to 300 dg/min, preferably 0.1 to 1.5 dg/min, preferably 0.15 to 1.0 dg/min, preferably 0.15 to 0.8 dg/min) (ASTM 1238, 2.16 kg, 230° C.). Alternately, the polymers produced herein may have a melt flow rate (MFR) of at least 0.01 dg/min (preferably 0.1 to 50 dg/min, preferably 1 to 10 dg/min).

Preferred polymers produced herein may be homopolymers or copolymers. In a preferred embodiment, the comonomer(s) are present at up to 50 mol %, preferably from 0.01 to 40 mol %, preferably 1 to 30 mol %, preferably from 5 to 20 mol %.

In useful embodiments, the polymers produced are propylene-ethylene copolymers having from 1 to 35 wt % ethylene (preferably 5 to 30, preferably 5 to 25) and 99 to 65 wt % propylene (preferably 95 to 70, preferably 95 to 75), with optional one or more diene present at up to 10 wt % (preferably from 0.00001 to 6.0 wt %, preferably from 0.002 to 5.0 wt %, preferably from 0.003 to 0.2 wt %), based upon weight of the copolymer. Non-limiting examples of useful dienes include, cyclopentadiene, norbornadiene, dicyclopentadiene, 5-ethylidene-2-norbornene ("ENB"), 5-vinyl-2-norbornene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1 and 9-methyl-1,9-decadiene.

In some embodiments herein, a multimodal polyolefin composition is produced, comprising a first polyolefin component and at least another polyolefin component, different from the first polyolefin component by molecular weight, preferably such that the GPC trace has more than one peak or inflection point.

The term "multimodal," when used to describe a polymer or polymer composition, means "multimodal molecular weight distribution," which is understood to mean that the Gel Permeation Chromatography (GPC) trace, plotted as Absorbance versus Retention Time (seconds), has more than one peak or at least one inflection points. An "inflection point" is that point where the second derivative of the curve changes in sign (e.g., from negative to positive or vice versa). For example, a polyolefin composition that includes a first lower molecular weight polymer component (such as a polymer having an Mw of 100,000 g/mol) and a second higher molecular weight polymer component (such as a polymer having an Mw of 300,000 g/mol) is considered to be a "bimodal" polyolefin composition. Preferably, the Mw's of the polymer or polymer composition differ by at least 10%, relative to each other, preferably by at least 20%, preferably at least 50%, preferably by at least 100%, preferably by a least 200%. Likewise, in a preferred embodiment, the Mw's of the polymer or polymer composition differ by 10% to 10,000%, relative to each other, preferably by 20% to 1000%, preferably 50% to 500%, preferably by at least 100% to 400%, preferably 200% to 300%.

Unless otherwise indicated, measurements of the moments of molecular weight, i.e., weight average molecular weight (Mw), number average molecular weight (Mn), and z average molecular weight (Mz) are determined by Gel Permeation Chromatography (GPC) as described in Macromolecules, 2001, Vol. 34, No. 19, pg. 6812, which is fully incorporated herein by reference, including that, a High Temperature Size Exclusion Chromatograph (SEC, Waters Alliance 2000), equipped with a differential refractive index detector (DRI) equipped with three Polymer Laboratories PLgel 10 mm Mixed-B columns is used. The instrument is operated with a flow rate of 1.0 cm3/min, and an injection volume of 300 µL. The various transfer lines, columns, and differential refractometer (the DRI detector) are housed in an oven maintained at 145° C. Polymer solutions are prepared by heating 0.75 to 1.5 mg/mL of polymer in filtered 1,2,4-Trichlorobenzene (TCB) containing ~1000 ppm of butylated hydroxy toluene (BHT) at 160° C. for 2 hours with continuous agitation. A sample of the polymer containing solution is injected into to the GPC and eluted using filtered 1,2,4-trichlorobenzene (TCB) containing ~1000 ppm of BHT. The separation efficiency of the column set is calibrated using a series of narrow MWD polystyrene standards reflecting the expected Mw range of the sample being analyzed and the exclusion limits of the column set. Seventeen individual polystyrene standards, obtained from Polymer Laboratories (Amherst, Mass.) and ranging from Peak Molecular Weight (Mp) ~580 to 10,000,000, were used to generate the calibration curve. The flow rate is calibrated for each run to give a common peak position for a flow rate marker (taken to be the positive inject peak) before determining the retention volume for each polystyrene standard. The flow marker peak position is used to correct the flow rate when analyzing samples. A calibration curve (log(Mp) vs. retention volume) is generated by recording the retention volume at the peak in the DRI signal for each PS standard, and fitting this data set to a 2nd-order polynomial. The equivalent polyethylene molecular weights are determined by using the Mark-Houwink coefficients shown in Table B.

TABLE B

Mark-Houwink coefficients

| Material | K (dL/g) | α |
|---|---|---|
| PS | $1.75 \times 10^{-4}$ | 0.67 |
| PE | $5.79 \times 10^{-4}$ | 0.695 |

In a preferred embodiment, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC and have a multi-modal, preferably bimodal, Mw/Mn.

In embodiments of the invention, the polymer produced is an ethylene polymer or a propylene polymer.

In embodiments of the invention, the polymer produced is a tactic polymer, preferably an isotactic or highly isotactic polymer. In embodiments of the invention, the polymer produced is isotactic polypropylene, such as highly isotactic polypropylene.

The term "isotactic polypropylene" (iPP) is defined as having at least 10% or more isotactic pentads. The term "highly isotactic polypropylene" is defined as having 50% or more isotactic pentads. The term "syndiotactic polypropylene" is defined as having 10% or more syndiotactic pentads. The term "random copolymer polypropylene" (RCP), also called propylene random copolymer, is defined to be a copolymer of propylene and 1 to 10 wt % of an olefin chosen from ethylene and $C_4$ to $C_8$ alpha-olefins. Preferably, isotactic polymers (such as iPP) have at least 20% (preferably at least 30%, preferably at least 40%) isotactic pentads. A polyolefin is "atactic," also referred to as "amorphous" if it has less than 10% isotactic pentads and syndiotactic pentads.

Polypropylene microstructure is determined by $^{13}$C-NMR spectroscopy, including the concentration of isotactic and syndiotactic diads ([m] and [r]), triads ([mm] and [rr]), and pentads ([mmmm] and [rrrr]). The designation "m" or "r" describes the stereochemistry of pairs of contiguous propylene groups, "m" referring to meso and "r" to racemic. Samples are dissolved in $d_2$-1,1,2,2-tetrachloroethane, and spectra recorded at 125° C. using a 100 MHz (or higher) NMR spectrometer. Polymer resonance peaks are referenced to mmmm=21.8 ppm. Calculations involved in the characterization of polymers by NMR are described by F. A. Bovey in POLYMER CONFORMATION AND CONFIGURATION (Academic Press, New York 1969) and J. Randall in POLYMER SEQUENCE DETERMINATION, $^{13}$C-NMR METHOD (Academic Press, New York, 1977).

End Uses

Articles made using polymers produced herein may include, for example, molded articles (such as containers and bottles, e.g., household containers, industrial chemical containers, personal care bottles, medical containers, fuel tanks, storageware, toys, sheets, pipes, and tubing) films, non-wovens, and the like. It should be appreciated that the list of applications above is merely exemplary, and is not intended to be limiting.

Experimental $^1$H NMR spectroscopic data were acquired at 250, 400, or 500 MHz using solutions prepared by dissolving approximately 10 mg of a sample in either $C_6D_6$, $CD_2Cl_2$, $CDCl_3$, or $D_8$-toluene. The chemical shifts (δ) presented are relative to the residual protium in the deuterated solvent at 7.15, 5.32, 7.24, and 2.09 for $C_6D_6$, $CD_2Cl_2$, $CDCl_3$, and $D_8$-toluene, respectively. For purposes of the claims 500 Mz and $CD_2Cl_2$ are used.

Hafnium complexes of a series of 2-((aminomethyl)phenyl)-8-anilinoquinoline ligands have been prepared and characterized. These complexes form active olefin polymerization catalysts when combined with activators, such as N,N-dimethylanilinium tetrakis(pentafluorophenyl)borate. Generic structures of the pre-catalyst complexes are shown below:

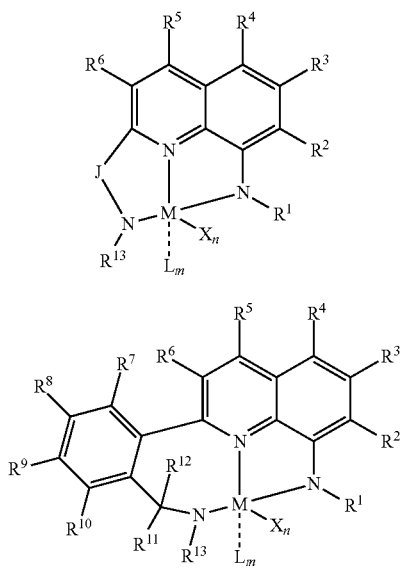

where dashed lines represent optional bonds and solid lines represent bonds. The J group is a three-atom-length bridge between the quinoline and the amido nitrogen (preferred J groups include arylmethyl and dihydro-1H-indenyl, and tetrahydronaphthalenyl groups); M is Hf; $R^2$ to $R^6$ are H; X is $NMe_2$, or Me; n is 2; y is 0 and L is not present; $R^1$ is 2,6-diisopropylphenyl; $R^{13}$ is 2-methyl phenyl, 2,6-dimethylphenyl, or phenyl; $R^{12}$ is H; $R^{11}$ is H or forms a ring with $R^{10}$; $R^9$ is H; $R^{10}$ is H or forms a ring with $R^{11}$, and $R^7$ and $R^8$ are each H or are joined together to form a six-membered aromatic ring.

Figure 2:
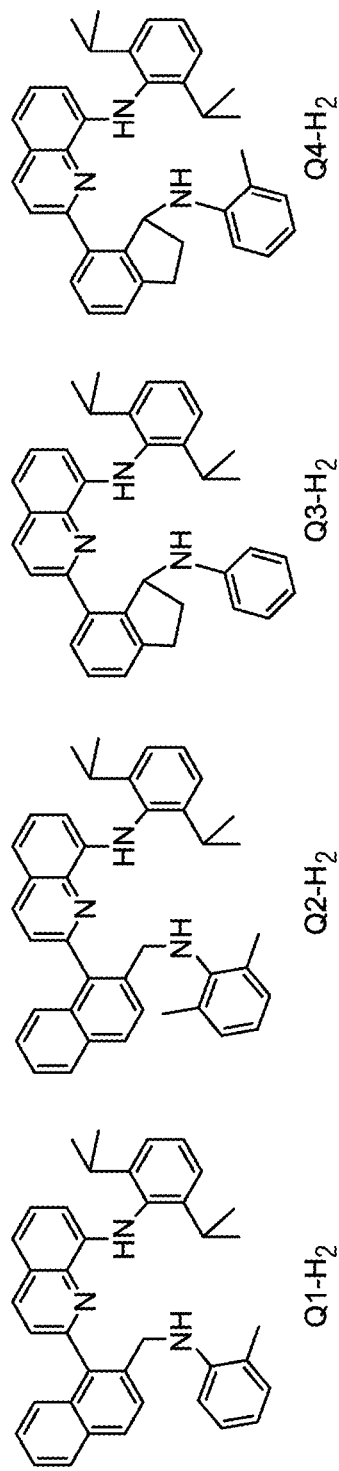
FIG. 2 shows examples of quinolinyldiamine ligands prepared in the Experimental section.
Figure 3:
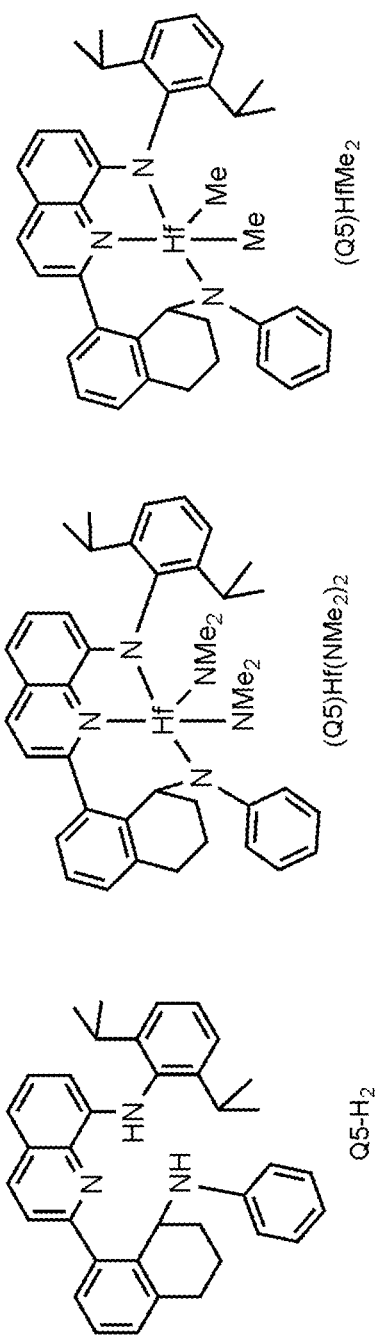
FIG. 3 shows drawings of quinolinyldiamide ligand and metal complex that contains a fused dihydronaphthalene linker group.
Figure 4:
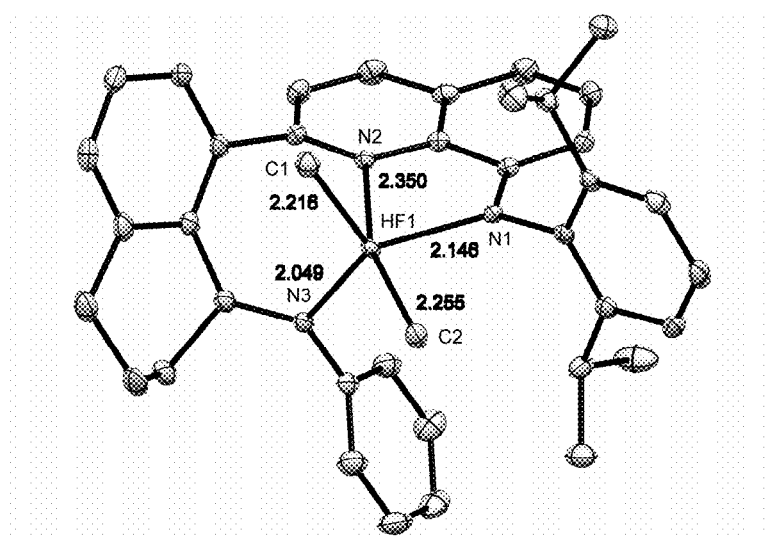
FIG. 4 shows the solid-state structure of $(Q5)HfMe_2$ as determined by single crystal X-ray diffraction.

Specific examples of quinolinyldiamine ligands that have been prepared are shown in FIG. 2. Specific examples of quinolinyldiamido complexes that have been prepared are shown in FIG. 1.

Synthesis of Ligands and Complexes 4,4,5,5-Tetramethyl-2-(2-methyl-1-naphthyl)-1,3,2-dioxaborolane 1,2-Dibromoethane (ca. 0.3 ml) was added to 6.10 g (250 mmol) of magnesium turnings in 1000 mL of THF. This mixture was stirred for 10 min, then 55.3 g (250 mmol) of 1-bromo-2-methylnaphthalene was added by vigorous stirring, and the resulting mixture was stirred for 3.5 hours at room temperature. Further on, 46.5 g (250 mmol) of 2-isopropoxy-4,4,5,5-tetramethyl-1,3,2-dioxaborolane was added in one portion. The obtained mixture was stirred for 15 min and then poured into 1000 mL of cold water. The product was extracted with 3×300 mL of ethyl acetate. The combined organic extract was washed by water, brine, then dried over $MgSO_4$, and, finally, evaporated to dryness. The resulting white solid was washed by 2×75 mL of pentane and dried in vacuum. Yield 47.3 g (70%). $^1$H NMR ($CDCl_3$): δ 8.12 (m, 1H, 8-H), 7.77 (m, 1H, 5-H), 7.75 (d, J=8.4 Hz, 1H, 4-H), 7.44 (m, 1H, 7-H), 7.38 (m, 1H, 6-H), 7.28 (d, J=8.4 Hz, 1H, 3-H), 2.63 (s, 3H, 2-Me), 1.48 (s, 12H, $CMe_2CMe_2$).

2-[2-(Bromomethyl)-1-naphthyl]-4,4,5,5-tetramethyl-1,3,2-dioxaborolane

A mixture of 47.3 g (176 mmol) of 4,4,5,5-tetramethyl-2-(2-methyl-1-naphthyl)-1,3,2-dioxaborolane, 33.0 g (185 mmol) of N-bromosuccinimide, and 0.17 g of benzoylperoxide in 340 mL of carbon tetrachloride was stirred at 75° C. for 14 hours. Further on, the reaction mixture was cooled to room temperature, filtered through glass frit (G3), and the filtrate was evaporated to dryness. This procedure gave 62.2 g (99%) of a beige solid. $^1$H NMR ($CDCl_3$): δ 8.30 (m, 1H, 8-H), 7.84 (d, J=8.3 Hz, 1H, 4-H), 7.79 (m, 1H, 5-H), 7.43-7.52 (m, 3H, 3,6,7-H), 4.96 (s, 2H, $CH_2Br$), 1.51 (s, 12H, $CMe_2CMe_2$).

2,6-Dimethyl-N-{[1-(4,4,5,5-tetramethyl-1,3,2-dioxaborolan-2-yl)-2-naphthyl]methyl}aniline A mixture of 10.5 g (86.4 mmol) of 2,6-dimethylaniline, 20.0 g (57.6 mmol) of 2-[2-(bromomethyl)-1-naphthyl]-4,4,5,5-tetramethyl-1,3,2-dioxaborolane, and 8.70 g (63.4 mmol) of $K_2CO_3$ in 400 mL of N,N-dimethylformamide (DMF) was stirred at 80° C. for 12 hours. The resulting mixture was poured into 1000 mL of water. Crude product was extracted with 3×200 mL of ethyl acetate. The combined extract was dried over $MgSO_4$ and then evaporated to dryness. An excess of aniline was distilled off using a Kugelrohr apparatus. The product was isolated by flash-chromatography on silica gel 60 (40-63 um; eluent: hexane-ethyl acetate=20:1, vol.). Yield 8.00 g (40%) of a yellow oil. $^1$H NMR ($CDCl_3$): δ 8.22 (d, J=8.3 Hz, 1H), 7.79 (d, J=8.3 Hz, 1H), 7.76 (d, J=8.5 Hz, 1H), 7.47 (m, 2H), 7.29 (d, J=8.3 Hz, 1H), 6.99 (d, J=7.5 Hz, 2H), 6.83 (m, 1H), 4.38 (s, 2H), 3.77 (br.s, 1H), 2.28 (s, 6H), 1.44 (s, 12H).

2-Methyl-N-{[1-(4,4,5,5-tetramethyl-1,3,2-dioxaborolan-2-yl)-2-naphthyl]methyl}aniline A mixture of 18.5 g (172 mmol) of 2-methylaniline, 40.0 g of 2-[2-(bromomethyl)-1-naphthyl]-4,4,5,5-tetramethyl-1,3,2-dioxaborolane, and 17.5 g (126 mmol) of $K_2CO_3$ in 500 mL of DMF was stirred in argon atmosphere for 12 hours at 80° C. The resulting mixture was poured into 1200 mL of water. Crude product was extracted with 3×200 mL of ethyl acetate. The combined organic extract was dried over $Na_2SO_4$ and then evaporated to dryness. The residue was recrystallized from a mixture of 300 mL of hexane and 20 mL of ethyl acetate. Yield 28.0 g (65%) of yellow crystals. $^1$H NMR ($CDCl_3$): δ 8.20 (m, 1H), 7.84 (d, J=8.5 Hz, 1H), 7.82 (m, 1H), 7.43-7.52 (m, 3H), 7.14 (m, 1H), 7.06 (m, 1H), 6.79 (m, 1H), 6.68 (m, 1H), 4.53 (s, 2H), 3.95 (br.s, 1H), 2.11 (s, 3H), 1.36 (s, 12H).

8-(2,6-Diisopropylphenylamino)quinolin-2(1H)-one

To a suspension of 5.63 g (140 mmol, 60% wt. in mineral oil) of NaH in 1000 mL of dry tetrahydrofuran (THF) was added 30.0 g (134 mmol) of 8-bromoquinolin-2(1H)-one in small portions at 0° C. After that the reaction mixture was stirred for 30 min at room temperature. The solution obtained was cooled to 0° C., and 20.2 g (134 mmol) of tert-butylchlorodimethylsilane was added in one portion. The resulting mixture was stirred for 30 min and then poured into 1 L of water. The protected 8-bromoquinolin-2(1H)-one was extracted with 3×400 mL of diethyl ether. The combined extract was dried over $Na_2SO_4$ and then evaporated to dryness. This procedure gave 45.2 g of the protected 8-bromoquinolin-2(1H)-one (99% purity by GC/MS) as a dark red oil. To a solution of 27.7 mL (147 mmol) of 2,6-diisopropylaniline in 1500 mL of dry toluene 60.5 mL (147 mmol) of 2.5 M n-butyllithium in hexanes was added at room temperature. The obtained suspension was heated to 100° C. and then cooled to room temperature. To the reaction mixture 2.45 g (2.68 mmol) of $Pd_2(dba)_3$, 2.55 g (5.36 mmol) of 2-dicyclohexylphosphino-2',4',6'-triisopropylbiphenyl (XPhos), and 45.2 g (134 mmol) of the protected 8-bromoquinolin-2(1H)-one were subsequently added. The dark brown suspension obtained was stirred at 60° C. till the lithium salt precipitate disappeared (approx. 30 minutes). The resulting dark red solution was quenched by 100 mL of water; the organic layer was separated, dried over $Na_2SO_4$, and then evaporated to dryness. The obtained oil was dissolved in a mixture of 1000 mL of dichloromethane and 500 mL of methanol followed by an addition of 50 mL of 12 M hydrochloric acid. The reaction mixture was stirred at room temperature for 3 hours, then poured into 2000 mL of 5% aqueous $K_2CO_3$. The product was extracted with 3×700 mL of dichloromethane. The combined extract was dried over $Na_2SO_4$ and then evaporated to dryness. The resulting solid was triturated with 300 mL of hexane and then filtered off on a glass frit (G3). Yield 34.1 g (79%) of a marsh-green solid. $^1$H NMR ($CDCl_3$): δ 13.29 (br.s, 1H), 7.80-7.81 (d, J=9.5 Hz, 1H), 7.35-7.38 (m, 1H), 7.29-7.30 (m, 3H), 6.91-6.95 (m, 2H), 6.58-6.60 (d, J=9.5 Hz, 1H), 6.27-6.29 (m, 1H), 3.21 (sept, J=6.9 Hz, 2H), 1.25-1.26 (d, J=6.9 Hz, 6H), 1.11-1.12 (d, J=6.9 Hz, 6H).

2-Chloro-N-(2,6-diisopropylphenyl)quinolin-8-amine 15.0 g (46.9 mmol) of 8-(2,6-diisopropylphenylamino)quinolin-2(1H)-one was added to 250 mL of phosphorus oxychloride in one portion. The resulting suspension was stirred for 40 hours at 105° C., then cooled to room temperature, and poured into 4000 mL of crushed ice. The product was extracted with 3×400 mL of diethyl ether. The combined extract was dried over $K_2CO_3$ and then evaporated to dryness. The resulting solid was triturated with 30 mL of cold hexane; the precipitate was filtered off on a glass frit (G3) and then dried in vacuum. Yield 15.7 g (100%) of a yellow-green solid. $^1$H NMR ($CDCl_3$): δ 8.04-8.05 (d, J=8.6 Hz, 1H), 7.38-7.39 (d, J=8.5 Hz, 1H), 7.33-7.36 (m, 1H), 7.22-7.27 (m, 4H), 7.04-7.06 (d, J=8.1 Hz, 1H), 6.27-6.29 (d, J=7.8 Hz, 1H), 3.20 (sept, J=6.9 Hz, 2H), 1.19-1.20 (d, J=6.9 Hz, 6H), 1.10-1.11 (d, J=6.9 Hz, 6H).

7-Bromoindan-1-ol

To a mixture of 100 g (746 mmol) of indan-1-ol, 250 mL (1.64 mol) of TMEDA, and 3000 mL of pentane cooled to −20° C. was added 655 mL (1.64 mol) of 2.5M "BuLi in hexanes. After that the reaction mixture was heated to reflux for 12 hours and then cooled to −80° C. Further on, 225 mL (1.87 mol) of 1,2-dibromotetrafluoroethane was added, and the resulting mixture was allowed to warm to room temperature. This mixture was stirred for 12 h, and then 100 mL of water was added. The formed mixture was diluted with 2 L of water, and the organic layer was separated. The aqueous layer was extracted with 3×400 mL of toluene. The combined organic extract was dried over $Na_2SO_4$ and evaporated to dryness. The residue was distilled using a Kugelrohr apparatus at 120° C.–140° C./1 mbar. The obtained yellow oil was dissolved in 50 mL of triethylamine, and the formed solution was added drop-wise to a stirred solution of 49.0 mL (519 mmol) of acetic anhydride and 4.21 g (34.5 mmol) of 4-(N,N-dimethylamino)pyridine (DMAP) in 70 mL of triethylamine. The resulting mixture was stirred for 5 min, then 1 L of water was added, and stirring was continued for 12 h. After that the reaction mixture was extracted with 3×200 mL of ethyl acetate. The combined organic extract was washed with aqueous $Na_2CO_3$, dried over $Na_2SO_4$, and evaporated to dryness. The residue was purified by flash chromatography on silica gel 60 (40-63 um; eluent: hexane-ethyl acetate=30:1, vol.). The isolated ester was dissolved in 1000 mL of methanol, and 50.5 g (900 mmol) of KOH was added. This mixture was refluxed for 3 hours, then cooled to room temperature and poured into 4000 mL of water. The title product was extracted with 3×300 mL of dichloromethane. The combined organic extract was dried over $Na_2SO_4$ and evaporated to dryness. Yield 41.3 g (26%) of a white crystalline solid. $^1$H NMR ($CDCl_3$): δ 7.34 (d, J=7.6 Hz, 1H, 6-H), 7.19 (d, J=7.4 Hz, 1H, 4-H), 7.12 (dd, J=7.6 Hz, J=7.4 Hz, 1H, 5-H), 5.33 (dd, J=2.6 Hz, J=6.9 Hz, 1H, 1-H), 3.18-3.26 (m, 1H, 3- or 3'-H), 3.09 (m, 2H, 3,3'-H), 2.73 (m, 2H, 2,2'-H).

7-Bromoindan-1-one

To a solution of 37.9 g (177 mmol) of 7-bromoindan-1-ol in 3500 mL of dichloromethane 194 g (900 mmol) of pyridinium chlorochromate was added. The resulting mixture was stirred at room temperature for 5 hours, then passed through a silica gel 50 (40-63 um) pad (ca. 500 ml), and the elute was evaporated to dryness. Yield 27.6 g (74%) of a white crystalline solid. $^1$H NMR ($CDCl_3$): δ 7.51 (m, 1H, 6-H), 7.36-7.42 (m, 2H, 4,5-H), 3.09 (m, 2H, 3,3'-H), 2.73 (m, 2H, 2,2'-H).

(7-Bromo-2,3-dihydro-1H-inden-1-yl)phenylamine

To a stirred solution of 10.4 g (112 mmol) of aniline in 60 mL of toluene was added 5.31 g (28.0 mmol) of $TiCl_4$ over 30 min at room temperature in argon atmosphere. The resulting mixture was stirred for 30 min at 90° C. followed by an addition of 6.00 g (28.0 mmol) of 7-bromoindan-1-one. Then it was stirred for 10 min at 90° C., poured into 500 mL of water, and crude product was extracted with 3×100 mL of ethyl acetate. The combined organic extract was dried over $Na_2SO_4$ and then evaporated to dryness. The residue was recrystallized from 10 mL of ethyl acetate at −30° C. The resulting crystalline solid filtered off (G3) and dried in vacuum was dissolved in 100 mL of methanol, and then 2.70 g (42.9 mmol) of $NaBH_3CN$ and 0.5 mL of glacial acetic acid were added. This mixture was refluxed for 3 h in argon atmosphere, then cooled to room temperature and evaporated to dryness. The residue was diluted with 200 mL of water, and crude product was extracted with 3×50 mL of ethyl acetate. The combined organic extract was dried over $Na_2SO_4$ and evaporated to dryness. The residue was purified by flash chromatography on silica gel 60 (40-63 um; eluent: hexane-ethyl acetate-triethylamine=100:10:1, vol.). Yield 5.50 g (68%) of a yellow oil. $^1$H NMR ($CDCl_3$): δ 7.38 (m, 1H), 7.22 (m, 3H), 7.15 (m, 1H), 6.75 (m, 1H), 6.69 (m, 2H), 4.94 (m, 1H), 3.82 (br.s, 1H), 3.17-3.26 (m, 1H), 2.92-2.99 (m, 2H), 2.22-2.37 (m, 2H).

(7-Bromo-2,3-dihydro-1H-inden-1-yl)(2-methylphenyl)amine

To a stirred solution of 30.4 g (284 mmol) of 2-methylaniline in 150 mL of toluene 13.5 g (71.0 mmol) of $TiCl_4$ was added for 30 min at room temperature in argon atmosphere. The resulting mixture was stirred for 30 min at 90° C. followed by an addition of 15.0 g (71.0 mmol) of 7-bromoindan-1-one. This mixture was stirred for 10 min at 90° C., then poured into 500 mL of water, and extracted with 3×200 mL of ethyl acetate. The combined organic extract was separated, dried over $Na_2SO_4$, and evaporated to dryness. The residue was re-crystallized from 30 mL of ethyl acetate at −30° C. The formed crystalline solid was filtered off (G3) and then dried in vacuum. After that, it was dissolved in 500 mL of methanol, then 8.34 g (132 mmol) of $NaBH_3CN$ and 2.0 mL of glacial acetic acid were added. The resulting mixture was refluxed for 3 h, then cooled to room temperature, and evaporated to dryness. The residue was diluted with 200 mL of water, and crude product was extracted with 3×100 mL of ethyl acetate. The combined organic extract was dried over $Na_2SO_4$ and evaporated to dryness. The residue was purified by flash chromatography on silica gel 60 (40-63 um; eluent: hexane-ethyl acetate-triethylamine=100:10:1, vol.). Yield 17.4 g (81%) of a yellow crystalline solid. $^1$H NMR ($CDCl_3$): δ 7.41 (m, 1H), 7.26 (m, 1H), 7.16-7.22 (m, 2H), 7.09 (m, 1H), 6.78 (m, 1H), 6.72 (m, 1H), 4.97-7.98 (m, 1H), 3.70 (br.s, 1H), 3.20-3.29 (m, 1H), 2.96-3.01 (m, 1H), 2.25-2.42 (m, 2H), 2.10 (s, 3H).

Phenyl[7-(4,4,5,5-tetramethyl-1,3,2-dioxaborolan-2-yl)-2,3-dihydro-1H-inden-1-yl]amine To a solution of 2.50 g (8.70 mmol) of (7-bromo-2,3-dihydro-1H-inden-1-yl)phenylamine in 50 mL of THF 3.50 mL (8.70 mmol) of 2.5 M n-BuLi in hexanes was added at −80° C. in argon atmosphere. The reaction mixture was then stirred for 1 hour at this temperature. Further on, 11.1 mL (17.8 mmol) of 1.7 M t-BuLi in pentane was added, and the reaction mixture was stirred for 1 h. Then, 3.23 g (17.4 mmol) of 2-isopropoxy-4,4,5,5-tetramethyl-1,3,2-dioxaborolane was added. After that the cooling bath was removed, and the resulting mixture was stirred for 1 hour at room temperature. To the formed mixture, 10 mL of water was added, and the obtained mixture was evaporated to dryness. The residue was diluted with 200 mL of water, and the title product was extracted with 3×50 mL of ethyl acetate. The combined organic extract was dried over $Na_2SO_4$ and evaporated to dryness. Yield 2.80 g (96%) of a light yellow oil. $^1$H NMR ($CDCl_3$): δ 7.63 (m, 1H), 7.37-7.38 (m, 1H), 7.27-7.30 (m, 1H), 7.18 (m, 2H), 6.65-6.74 (m, 3H), 5.20-5.21 (m, 1H), 3.09-3.17 (m, 1H), 2.85-2.92 (m, 1H), 2.28-2.37 (m, 1H), 2.13-2.19 (m, 1H), 1.20 (s, 6H), 1.12 (s, 6H).

(2-Methylphenyl)[7-(4,4,5,5-tetramethyl-1,3,2-dioxaborolan-2-yl)-2,3-dihydro-1H-inden-1-yl]amine To a solution of 17.4 g (57.6 mmol) of (7-bromo-2,3-dihydro-1H-inden-1-yl)(2,6-dimethylphenyl)amine in 350 mL of THF was added 23.0 mL (57.6 mmol) of 2.5M n-BuLi in hexanes at −80° C. in argon atmosphere. The reaction mixture was then stirred for 1 hour at this temperature. Further on, 74.0 mL (118 mmol) of 1.7 M t-BuLi in pentane was added, and the reaction mixture was stirred for 1 hour. Then, 21.4 g (115 mmol) of 2-isopropoxy-4,4,5,5-tetramethyl-1,3,2-dioxaborolane was added. Thereafter, the cooling bath was removed, and the resulting mixture was stirred for 1 hour at room temperature. Then, 10 mL of water was added, and this mixture was evaporated to dryness. The residue was diluted with 200 mL of water, and the title product was extracted with 3×50 mL of ethyl acetate. The combined organic extract was dried over $Na_2SO_4$ and then evaporated to dryness. Yield 17.1 g (85%) of a light yellow oil. $^1$H NMR ($CDCl_3$): δ 7.72 (d, J=7.1 Hz, 1H), 7.45 (d, J=7.3 Hz, 1H), 7.35 (dd, J=7.1 Hz, J=7.3 Hz, 1H), 7.21-7.26 (m, 1H), 7.08 (d, J=7.1 Hz, 1H), 6.90 (d, J=8.1 Hz, 1H), 6.72 (m, 1H), 5.29 (m, 1H), 3.70 (m, 1H), 3.18-3.27 (m, 1H), 2.92-3.00 (m, 1H), 2.67-2.75 (m, 2H), 2.22-2.27 (m, 1H), 2.06 (s, 3H), 1.23 (s, 6H), 1.14 (s, 6H).

N-(2,6-Diisopropylphenyl)-2-{2-[(o-tolylamino)methyl]naphthalen-1-yl}quinolin-8-amine (Q1-H$_2$)

To a solution of 540 mg (1.59 mmol) of 2-chloro-N-(2,6-diisopropylphenyl)quinolin-8-amine in 50 mL of dioxane was added 476 mg (1.28 mmol) of 2-methyl-N-{[1-(4,4,5,5-tetramethyl-1,3,2-dioxaborolan-2-yl)-2-naphthyl]methyl}aniline. Then 1.30 g (3.98 mmol) of cesium carbonate and 15 mL of water were subsequently added. The obtained mixture was purged with argon followed by an addition of 92 mg (0.08 mmol) of $Pd(PPh_3)_4$. This mixture was stirred for 2 h at 90° C., then cooled to room temperature. To the obtained two-phase mixture was added 100 mL of hexane, and the organic layer was separated, washed with brine, dried over $Na_2SO_4$, and then evaporated to dryness. The residue was purified by flash chromatography on silica gel 60 (40-63 um; eluent: hexane-ethyl acetate-triethylamine=100:5:1, vol.) and then recrystallized from 25 mL of hexane. Yield 650 mg (93%) of a yellow powder. $^1$H NMR ($CDCl_3$): δ 8.22-8.23 (d, J=8.2 Hz, 1H), 7.95-7.96 (d, J=8.5 Hz, 1H), 7.91-7.93 (d, J=8.0 Hz, 1H), 7.73-7.75 (d, J=8.5 Hz, 1H), 7.58-7.61 (m, 3H), 7.50 (t, J=7.6 Hz, 1H), 7.40 (t, J=7.8 Hz, 1H), 7.30-7.32 (m, 2H), 7.22-7.25 (m, 2H), 7.15-7.17 (d, J=8.0 Hz, 1H), 6.98-7.01 (m, 2H), 6.60 (t, J=7.4 Hz, 1H), 6.51-6.52 (d, J=7.8 Hz, 1H), 6.31-6.32 (d, J=7.8 Hz, 1H), 4.41-4.50 (m, 2H), 3.82 (br.s, 1H), 3.19-3.30 (m, 2H), 2.05 (s, 3H), 1.07-1.14 (m, 12H).

N-(2,6-Diisopropylphenyl)-2-{2-[(2,6-dimethylphenylamino)methyl]naphthalen-1-yl}quinolin-8-amine (Q2-H$_2$)

To a solution of 1.95 g (5.73 mmol) of 2-chloro-N-(2,6-diisopropylphenyl)quinolin-8-amine in 125 mL of dioxane was added 2.00 g (5.15 mmol) of 2,6-dimethyl-N-{[1-(4,4,5,5-tetramethyl-1,3,2-dioxaborolan-2-yl)-2-naphthyl]methyl}aniline. Then 4.70 g (14.4 mmol) of cesium carbonate and 50 mL of water were subsequently added. The mixture obtained was purged with argon followed by an addition of 330 mg (0.30 mmol) of $Pd(PPh_3)_4$. This mixture was stirred for 2 hours at 90° C., then cooled to room temperature. To the obtained two-phase mixture was added 200 mL of hexane. The organic layer was separated, washed with brine, dried over $Na_2SO_4$, and then evaporated to dryness. The residue was purified by flash chromatography on silica gel 60 (40-63 um; eluent: hexane-ethyl acetate-triethylamine=100:5:1, vol.) and then recrystallized from 50 mL of hexane. Yield 1.54 g (48%) of a yellow powder. $^1$H NMR ($CDCl_3$): δ 8.19-8.21 (d, J=8.3 Hz, 1H), 7.91-7.94 (m, 2H), 7.61-7.63 (d, J=8.5 Hz, 1H), 7.47-7.56 (m, 4H), 7.38-7.41 (m, 1H), 7.28-7.34 (m, 2H), 7.17-7.22 (m, 3H), 6.87-6.89 (d, J=7.5 Hz, 2H), 6.76-6.80 (m, 1H), 6.31-6.33 (d, J=7.5 Hz, 1H), 4.07-4.20 (m, 2H), 3.39 (br.s, 1H), 3.15-3.24

(m, 2H), 2.00 (s, 6H), 1.10-1.12 (d, J=6.5 Hz, 3H), 1.07-1.08 (d, J=6.9 Hz, 3H), 1.03-1.04 (d, J=6.7 Hz, 3H), 0.96-0.98 (d, J=6.3 Hz, 3H).

N-(2,6-Diisopropylphenyl)-2-[3-(phenylamino)-2,3-dihydro-1H-inden-4-yl]quinolin-8-amine (Q3-H$_2$)

To a solution of 4.63 g (13.6 mmol) of 2-chloro-N-(2,6-diisopropylphenyl)quinolin-8-amine in 250 mL of dioxane was added 4.10 g (12.3 mmol) of phenyl[7-(4,4,5,5-tetramethyl-1,3,2-dioxaborolan-2-yl)-2,3-dihydro-1H-inden-1-yl]amine. Then 11.1 g (34.0 mmol) of cesium carbonate and 80 mL of water were subsequently added. The mixture obtained was purged with argon followed by an addition of 790 mg (0.68 mmol) of Pd(PPh$_3$)$_4$. This mixture was stirred for 2 hours at 90° C., then cooled to room temperature. To the obtained two-phase mixture was added 300 mL of hexane, and the organic layer was separated, washed with brine, dried over Na$_2$SO$_4$, and then evaporated to dryness. The residue was purified by flash chromatography on silica gel 60 (40-63 um; eluent: hexane-ethyl acetate-triethylamine=100:5:1, vol.) and then recrystallized from 150 mL of hexane. Yield 2.15 g (34%) of a yellow powder. $^1$H NMR (CDCl$_3$): δ 8.01-8.03 (d, J=8.5 Hz, 1H), 7.87-7.89 (d, J=8.5 Hz, 1H), 7.77-7.78 (d, J=7.3 Hz, 1H), 7.66 (br.s, 1H), 7.41-7.49 (m, 2H), 7.32-7.36 (m, 1H), 7.25-7.28 (m, 2H), 7.21 (t, J=7.9 Hz, 1H), 7.01-7.09 (m, 3H), 6.63 (t, J=7.3 Hz, 1H), 6.48-6.50 (d, J=7.7 Hz, 2H), 6.24-6.26 (d, J=7.7 Hz, 1H), 5.40-5.48 (m, 1H), 3.80-3.85 (m, 1H), 3.17-3.31 (m, 3H), 2.94-3.01 (m, 1H), 2.26-2.39 (m, 2H), 1.13-1.23 (m, 12H).

N-(2,6-Diisopropylphenyl)-2-[3-(o-tolylamino)-2,3-dihydro-1H-inden-4-yl]quinolin-8-amine (Q4-H$_2$)

To a solution of 3.94 g (11.6 mmol) of 2-chloro-N-(2,6-diisopropylphenyl)quinolin-8-amine in 250 mL of dioxane was added 3.66 g (10.5 mmol) of (2-methylphenyl)[7-(4,4,5,5-tetramethyl-1,3,2-dioxaborolan-2-yl)-2,3-dihydro-1H-inden-1-yl]amine. Then 9.50 g (29.0 mmol) of cesium carbonate and 80 mL of water were subsequently added. The mixture obtained was purged with argon followed by an addition of 670 mg (0.58 mmol) of Pd(PPh$_3$)$_4$. This mixture was stirred for 2 hours at 90° C., then cooled to room temperature. To the obtained two-phase mixture was added 300 mL of hexane. The hexane layer was separated, washed with brine, dried over Na$_2$SO$_4$, and then evaporated to dryness. The residue was purified by flash chromatography on silica gel 60 (40-63 um; eluent: hexane-ethyl acetate-triethylamine=100:5:1, vol.) and then recrystallized from 100 mL of hexane. Yield 3.80 g (69%) of a yellow powder. $^1$H NMR (CDCl$_3$): δ 7.95-7.97 (d, J=8.7 Hz, 1H), 7.76-7.78 (d, J=8.7 Hz, 2H), 7.66 (br.s, 1H), 7.42-7.50 (m, 2H), 7.18-7.37 (m, 5H), 7.05-7.09 (m, 1H), 6.99-7.01 (d, J=8.1 Hz, 1H), 6.90-6.92 (d, J=7.1 Hz, 1H), 6.68-6.70 (d, J=7.9 Hz, 1H), 6.59 (t, J=7.1 Hz, 1H), 6.24-6.26 (d, J=6.9 Hz, 1H), 5.48-5.51 (m, 1H), 3.61-3.63 (d, J=6.7 Hz, 1H), 3.17-3.31 (m, 3H), 2.97-3.05 (m, 1H), 2.44-2.53 (m, 1H), 2.20-2.27 (m, 1H), 1.67 (s, 3H), 1.22-1.24 (d, J=6.7 Hz, 3H), 1.17-1.19 (d, J=6.7 Hz, 3H), 1.14-1.16 (d, J=6.9 Hz, 3H), 1.11-1.12 (d, J=6.7 Hz, 3H).

Complex (Q1)Hf(NMe$_2$)$_2$.

Decane (12 mL) was added to Q1-H$_2$ (0.304 g, 0.553 mmol) and Hf(NMe$_2$)$_4$ (0.206 g, 0.581 mmol) and the mixture was warmed to 165° C. for 1 hour. The volatiles were removed by evaporation to afford a red solid that was washed with pentane (5 mL) and dried. Yield: 0.37 g, 82%.

Complex (Q1)HfMe$_2$.

Toluene (8 mL) was added to (Q1)Hf(NMe$_2$)$_2$ (0.370 g, 0.454 mmol) to form a solution. Trimethylaluminum (0.294 g, 4.08 mmol) dissolved in toluene (2 mL) was added and the mixture was warmed to 60° C. After 3 hours the volatiles were evaporated using a stream of nitrogen. The red solid was washed with pentane (5 mL) and dried. Yield: 0.2 g, 58%.

Complex (Q2)Hf(NMe$_2$)$_2$.

To a solution of 207 mg (0.36 mmol) of Q2-H$_2$ in 10 mL of decane was added 134 mg (0.37 mmol) of Hf(NMe$_2$)$_4$. The suspention was heated to 165° C. to dissolve the solids. The temperature was lowered to 100° C. and stirred for 12 hours. The solvents were evaporated until solids began to form and then cooled to room temperature. The resulting solids were filtered off and washed with pentane. Yield 122 mg (40%) as a red powder.

Complex (Q2)HfMe$_2$.

To a solution of 219 mg (0.26 mmol) of (Q2)Hf(NMe$_2$)$_2$ in 5 mL of toluene was added 172 mg (2.39 mmol) of AlMe$_3$ in a 20% wt solution of toluene. The solution was stirred at 60° C. for 5 hours. Then the solvents were evaporated to near dryness and 4 mL of pentane was added. The resulting red solid was filtered and washed with pentane. Yield 103 mg (50%) as a red powder. $^1$H NMR (C$_6$D$_6$): δ 7.73 (d, 1H), 7.62 (m, 2H), 7.51 (d, 1H), 7.34-7.05 (m, 9H), 6.96-6.90 (m, 2H), 6.81 (d, 1H), 6.28 (d, 1H), 4.41 (d, 1H), 3.86 (d, 1H), 3.67 (sept, 1H), 3.10 (sept, 1H), 2.75 (s, 3H), 1.72 (s, 3H), 1.21 (m, 6H), 0.914 (t, 6H), 0.06 (s, 3H), −0.36 (s, 3H).

Complex (Q3)Hf(NMe$_2$)$_2$.

To a solution of 221 mg (0.43 mmol) of Q3-H$_2$ in 10 ml of decane was added 164 mg (0.46 mmol) of Hf(NMe$_2$)$_4$. The suspention was heated to 165° C. and stirred for 10 min. The heat was reduced to 100° C. and stirred for an additional 5 min, at which time, red solids were seen. The suspention was cooled to room temperature, the solids filtered off and washed with pentane. Yield 225 mg (76%) as a red powder.

Complex (Q3)HfMe$_2$.

To a solution of 101 mg (0.13 mmol) of (Q3)Hf(NMe$_2$)$_2$ in 3 ml of toluene was added 88.0 mg (1.22 mmol) of AlMe$_3$ in a 20% by wt solution of toluene. The solution was stirred at 50° C. for 1 hour. Then the solvents were evaporated to near dryness and 4 mL of pentane was added. The resulting red solid was filtered and washed with pentane. Yield 45.0 mg (48%) as a red powder. $^1$H NMR (C$_6$D$_6$): δ 7.67 (d, 1H), 7.34-6.86 (m, 13H), 6.75 (d, 1H), 6.19 (d, 1H), 4.84 (d, 1H), 3.68 (sept, 1H), 3.2 (m, 1H), 2.70 (sept, 1H), 2.46 (q, 1H), 1.95 (q, 1H), 1.40 (m, 1H), 1.34 (d, 3H), 1.07 (d, 3H), 0.92 (d, 3H), 0.78 (d, 3H), 0.34 (s, 3H), −0.05 (s, 3H).

Complex (Q4)Hf(NMe$_2$)$_2$.

To a solution of 211 mg (0.40 mmol) of Q4-H$_2$ in 10 mL of decane was added 148 mg (0.41 mmol) of Hf(NMe$_2$)$_4$. The suspention was heated to 165° C. to dissolve the solids. The temperature was lowered to 100° C. and stirred for 12 hours. The solvents were evaporated until solids began to form and cooled to room temperature. The resulting solids were filtered off and washed with pentane. Yield 233 mg (73%) as a red powder.

Complex (Q4)HfMe$_2$.

To a solution of 101 mg (0.13 mmol) of (Q4)Hf(NMe$_2$)$_2$ in 5 ml of toluene was added 82.0 mg (1.13 mmol) of AlMe$_3$ in a 20% by wt solution of toluene. The solution was stirred at 55° C. for 2 hours. Then the solvents were evaporated to near dryness and 4 ml of pentane was added. The resulting red solid was filtered and washed with pentane. Yield 38.4 mg (41%) as a red powder. $^1$H NMR spectroscopic data shows broad resonances that suggests the presence of rotational isomers that are interconverting on the time scale of the data acquisition.

8-Bromo-1,2,3,4-tetrahydronaphthalen-1-ol

To a mixture of 78.5 g (530 mmol) of 1,2,3,4-tetrahydronaphthalen-1-ol, 160 mL (1.06 mol) of N,N,N',N'-tetramethylethylenediamine, and 3000 mL of pentane cooled to −20° C. 435 mL (1.09 mol) of 2.5 M "BuLi in hexanes was added dropwise. The obtained mixture was refluxed for 12 h, then cooled to −80° C., and 160 mL (1.33 mol) of 1,2-dibromotetrafluoroethane was added. The obtained mixture was allowed to warm to room temperature and then stirred for 12 h at this temperature. Thereafter, 100 mL of water was added. The resulting mixture was diluted with 2000 mL of water, and the organic layer was separated. The aqueous layer was extracted with 3×400 mL of toluene. The combined organic extract was dried over $Na_2SO_4$ and then evaporated to dryness. The residue was distilled using the Kugelrohr apparatus, b.p. 150-160° C./1 mbar. The obtained yellow oil was dissolved in 100 mL of triethylamine, and the formed solution was added dropwise to a stirred solution of 71.0 mL (750 mmol) of acetic anhydride and 3.00 g (25.0 mmol) of DMAP in 105 mL of triethylamine. The formed mixture was stirred for 5 min, then 1000 mL of water was added, and the obtained mixture was stirred for 12 h. Thereafter, the reaction mixture was extracted with 3×200 mL of ethyl acetate. The combined organic extract was washed with aqueous $Na_2CO_3$, dried over $Na_2SO_4$, and then evaporated to dryness. The residue was purified by flash chromatography on silica gel 60 (40-63 um, eluent: hexane-ethyl acetate=30:1, vol.). The isolated ester was dissolved in 1500 mL of methanol, 81.0 g (1.45 mol) of KOH was added, and the obtained mixture was heated to reflux for 3 h. The reaction mixture was then cooled to room temperature and poured into 4000 mL of water. The title product was extracted with 3×300 mL of dichloromethane. The combined organic extract was dried over $Na_2SO_4$ and then evaporated to dryness. Yield 56.0 g (47%) of a white crystalline solid. $^1$H NMR ($CDCl_3$): δ 7.38-7.41 (m, 1H, 7-H); 7.03-7.10 (m, 2H, 5,6-H); 5.00 (m, 1H, 1-H), 2.81-2.87 (m, 1H, 4/4'-H), 2.70-2.74 (m, 1H, 4'/4-H), 2.56 (br.s., 1H, OH), 2.17-2.21 (m, 2H, 2,2'-H), 1.74-1.79 (m, 2H, 3,3'-H).

8-Bromo-3,4-dihydronaphthalen-1(2H)-one

To a solution of 56.0 g (250 mmol) of 8-bromo-1,2,3,4-tetrahydronaphthalen-1-ol in 3500 mL of dichloromethane was added 265 g (1.23 mol) of pyridinium chlorochromate (PCC). The resulting mixture was stirred for 5 h at room temperature, then passed through a pad of silica gel 60 (500 mL; 40-63 um), and finally evaporated to dryness. Yield 47.6 g (88%) of a colorless solid. $^1$H NMR ($CDCl_3$): δ 7.53 (m, 1H, 7-H); 7.18-7.22 (m, 2H, 5,6-H); 2.95 (t, J=6.1 Hz, 2H, 4,4'-H); 2.67 (t, J=6.6 Hz, 2H, 2,2'-H); 2.08 (quint, J=6.1 Hz, J=6.6 Hz, 2H, 3,3'-H).

(8-Bromo-1,2,3,4-tetrahydronaphthalen-1-yl)phenylamine

To a stirred solution of 21.6 g (232 mmol) of aniline in 140 mL of toluene was added 10.93 g (57.6 mmol) of $TiCl_4$ over 30 min at room temperature under argon atmosphere. The resulting mixture was stirred for 30 min at 90° C. followed by an addition of 13.1 g (57.6 mmol) of 8-bromo-3,4-dihydronaphthalen-1(2H)-one. This mixture was stirred for 10 min at 90° C., then cooled to room temperature, and poured into 500 mL of water. The product was extracted with 3×50 mL of ethyl acetate. The combined organic extract was dried over $Na_2SO_4$, evaporated to dryness, and the residue was re-crystallized from 10 mL of ethyl acetate. The obtained crystalline solid was dissolved in 200 mL of methanol, 7.43 g (118 mmol) of $NaBH_3CN$ and 3 mL of acetic acid were added in argon atmosphere. This mixture was heated to reflux for 3 h, then cooled to room temperature, and evaporated to dryness. The residue was diluted with 200 mL of water, and crude product was extracted with 3×100 mL of ethyl acetate. The combined organic extract was dried over $Na_2SO_4$ and evaporated to dryness. The residue was purified by flash chromatography on silica gel 60 (40-63 um, eluent: hexane-ethyl acetate-triethylamine=100:10:1, vol.). Yield: 13.0 g (75%) of a yellow oil. Anal. Calc. for $C_{16}H_{16}BrN$: C, 63.59; H, 5.34; N, 4.63. Found: C, 63.82; H, 5.59; N, 4.49. $^1$H NMR ($CDCl_3$): δ 7.44 (m, 1H), 7.21 (m, 2H), 7.05-7.11 (m, 2H), 6.68-6.73 (m, 3H), 4.74 (m, 1H), 3.68 (br.s, 1H, NH), 2.84-2.89 (m, 1H), 2.70-2.79 (m, 1H), 2.28-2.32 (m, 1H), 1.85-1.96 (m, 1H), 1.76-1.80 (m, 1H), 1.58-1.66 (m, 1H).

N-Phenyl-8-(4,4,5,5-tetramethyl-1,3,2-dioxaborolan-2-yl)-1,2,3,4-tetrahydronaphthalen-1-amine To a solution of 13.0 g (43.2 mmol) of (8-bromo-1,2,3,4-tetrahydronaphthalen-1-yl)phenylamine in 250 mL THF was added 17.2 mL (43.0 mmol) of 2.5 M "BuLi at −80° C. Further on, this mixture was stirred for 1 h at this temperature, and 56.0 mL (90.3 mmol) of 1.6 M $^t$BuLi in pentane was added. The resulting mixture was stirred for 1 h at the same temperature. Then, 16.7 g (90.0 mmol) of 2-isopropoxy-4,4,5,5-tetramethyl-1,3,2-dioxaborolane was added. Thereafter, the cooling bath was removed, and the resulting mixture was stirred for 1 h at room temperature. Finally, 10 mL of water was added, and the obtained mixture was evaporated to dryness. The residue was diluted with 200 mL of water, and crude product was extracted with 3×100 mL of ethyl acetate. The combined organic extract was dried over $Na_2SO_4$ and then evaporated to dryness. Yield 15.0 g (98%) of a yellow oil. Anal. Calc. for $C_{22}H_{28}BNO_2$: C, 75.65; H, 8.08; N, 4.01. Found: C, 75.99; H, 8.32; N, 3.79. $^1$H NMR ($CDCl_3$): δ 7.59 (m, 1H), 7.18-7.23 (m, 4H), 6.71-6.74 (m, 3H), 5.25 (m, 1H), 3.87 (br.s, 1H, NH), 2.76-2.90 (m, 2H), 2.12-2.16 (m, 1H), 1.75-1.92 (m, 3H), 1.16 (s, 6H), 1.10 (s, 6H).

2-(8-Anilino-5,6,7,8-tetrahydronaphthalen-1-yl)-N-(2,6-diisopropylphenyl)quinolin-8-amine (Q5-H$_2$)

To a solution of 13.8 g (41.0 mmol) of 2-chloro-N-(2,6-diisopropylphenyl)quinolin-8-amine in 700 mL of 1,4-dioxane were added 15.0 g (43.0 mmol) of N-phenyl-8-(4,4,5,5-tetramethyl-1,3,2-dioxaborolan-2-yl)-1,2,3,4-tetrahydronaphthalen-1-amine, 35.0 g (107 mmol) of cesium carbonate and 400 mL of water. The obtained mixture was purged with argon for 10 min followed by an addition of 2.48 g (2.15 mmol) of $Pd(PPh_3)_4$. The formed mixture was stirred for 2 h at 90° C., then cooled to room temperature. To the obtained two-phase mixture 700 mL of n-hexane was added. The organic layer was separated, washed with brine, dried over $Na_2SO_4$, and then evaporated to dryness. The residue was purified by flash chromatography on silica gel 60 (40-63 um, eluent: hexane-ethyl acetate-triethylamine=100:5:1, vol.) and then re-crystallized from 150 mL of n-hexane. Yield 15.1 g (70%) of a yellow powder. Anal. calc. for $C_{37}H_{39}N_3$: C, 84.53; H, 7.48; N, 7.99. Found: C, 84.60; H, 7.56; N, 7.84. $^1$H NMR ($CDCl_3$): δ 7.85-7.87 (d, J=7.98 Hz, 1H), 7.56 (br.s, 1H), 7.43-7.45 (d, J=8.43 Hz, 1H), 7.21-7.38 (m, 6H), 7.12 (t, J=7.77 Hz, 1H), 6.87-6.89 (d, J=7.99 Hz, 1H), 6.74 (t, J=7.99 Hz, 1H), 6.36 (t, J=7.32 Hz, 1H), 6.14-6.21 (m, 3H), 5.35 (br.s, 1H), 3.56 (br.s, 1H), 3.20-3.41 (m, 2H), 2.83-2.99 (m, 2H), 2.10-2.13 (m, 1H), 1.77-1.92 (m, 3H), 1.13-1.32 (m, 12H).

Complex (Q5)HfMe$_2$.

Benzene (50 mL) was added to Q5-H$_2$ (2.21 g, 4.20 mmol) and Hf(NMe$_2$)$_4$ (1.58 g, 4.45 mmol) to form a clear orange solution. The mixture was heated to reflux for 16 hours to form a clear red-orange solution. Most of the volatiles were removed by evaporation under a stream of nitrogen to afford a concentrated red solution (ca. 5 mL) that was warmed to 40° C. Then hexane (30 mL) was added and the mixture was stirred to cause orange crystalline solid to form. This slurry was cooled to −40° C. for 30 minutes then the solid was collected by filtration and washed with additional cold hexane (2×10 mL). The resulting orange solid of (Q5)Hf(NMe$_2$)$_2$ was dried under reduced pressure (2.90 g, 3.67 mmol, 87.4% yield). This solid was dissolved in toluene (25 mL) and Me$_3$Al (12.8 mL, 25.6 mmol) was added. The mixture was warmed to 40° C. for 1 hour then evaporated under a stream of nitrogen. The crude product (2.54 g) was ~90% pure by HNMR spectroscopy. The solid was purified by recrystallization from CH$_2$Cl$_2$-hexanes (20 mL-20 mL) by slow evaporation to give pure product as orange crystals (1.33 g, 43.2% from ligand). The mother liquor was further concentrated for a second crop (0.291 g, 9.5% from ligand).

Complex (Q3)Zr(NMe$_2$)$_2$.

Decane (10 mL) was added to Q3-H$_2$ (0.102 g, 0.20 mmol) and Zr(NMe$_2$)$_4$ (0.055 g, 0.21 mmol). The mixture was heated to 100° C. overnight. The volatiles were then removed under a stream of nitrogen and the residue was washed with pentane (3 mL). Yield: 0.95 g, 69%.

Complex (Q3)ZrMe$_2$.

Toluene (4 mL) was added to (Q3)Zr(NMe$_2$)$_2$ (0.026 g, 0.037 mmol) to form a solution. Trimethylaluminum (0.027 g, 0.38 mmol) in toluene (3 mL) was added and the mixture was stirred for 1 hour. The volatiles were removed under a stream of nitrogen. The resulting solid was recrystallized from pentane at −40° C. Yield: 6.0 mg, 26%.

Olefin Polymerizations in Parallel Pressure Reactor

Catalyst screening for olefin polymerizations was performed in a parallel, pressure reactor (PPR) as generally described in U.S. Pat. No. 6,306,658; U.S. Pat. No. 6,455,316; U.S. Pat. No. 6,489,168; WO 00/09255; and J. Am. Chem. Soc., 2003, 125, pp. 4306-4317, each of which is fully incorporated herein by reference to the extent not inconsistent with this specification. Catalysts are screened in the PPR for their ability to produce a variety of polymers, including homopolyethylene, homopolypropylene, ethylene-hexene copolymer, ethylene-octene copolymer, and ethylene-propylene copolymer. The following describes a general procedure used to screen catalysts. The desired temperatures, pressures, quantities of chemicals used (e.g., pre-catalysts, activators, scavengers, etc.) will vary from experiment to experiment, and specific values are given in the Table (or immediately above or below the Table) where data are presented.

A pre-weighed glass vial insert and disposable stirring paddle were fitted to each reaction vessel of the reactor, which contains 48 individual reaction vessels. The reactor was purged with the gaseous monomer (typically ethylene or propylene) to be used for the polymerization. If desired, liquid comonomer (typically 1-octene or 1-hexene) was then injected into each reaction vessel through a valve, followed by enough solvent (typically isohexane) to bring the total reaction volume, including the subsequent additions, to the desired volume (typically 5 mL). The reactor was then closed and each vessel was individually heated and pressurized with gaseous monomer to the targeted temperature and pressure. The contents of the vessel were then stirred at 800 rpm. A solution of scavenger (typically an organoaluminum reagent in isohexane or toluene) was then added along with a solvent chaser (typically 500 microliters). An activator solution in toluene (typically 1.1 molar equivalent relative to the pre-catalyst complex) was then injected into the reaction vessel along with a solvent chaser (typically 500 microliters). Then a toluene solution of the dissolved pre-catalyst complex was added along with a solvent chaser (typically 500 microliters).

The reaction was then allowed to proceed until either a set amount of pressure had been taken up by the polymerization (typically 12 psi=0.137 MPa for ethylene-octene copolymerizations performed at 75 psi, typically 6 psi=0.069 MPa for propylene polymerizations performed at 100 psi) or a set amount of time had passed (typically 30 minutes). At this point, the reaction was quenched by pressurizing the vessel with compressed air or carbon dioxide. After the polymerization reaction, the glass vial insert containing the polymer product and solvent was removed from the reactor and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight.

To determine various molecular weight related values by GPC, high temperature size exclusion chromatography was performed using an automated "Rapid GPC" system as generally described in U.S. Pat. No. 6,491,816; U.S. Pat. No. 6,491,823; U.S. Pat. No. 6,475,391; U.S. Pat. No. 6,461,515; U.S. Pat. No. 6,436,292; U.S. Pat. No. 6,406,632; U.S. Pat. No. 6,175,409; U.S. Pat. No. 6,454,947; U.S. Pat. No. 6,260,407; and U.S. Pat. No. 6,294,388. This apparatus has a series of three 30 cm×7.5 mm linear columns, each containing PLgel 10 um, Mix B. The GPC system was calibrated using polystyrene standards ranging from 580 g/mol-3,390,000 g/mol. The system was operated at an eluent flow rate of 2.0 mL/min and an oven temperature of 165° C. 1,2,4-trichlorobenzene was used as the eluent. The polymer samples were dissolved in 1,2,4-trichlorobenzene at a concentration of 0.1-0.9 mg/mL. 250 µL of a polymer solution was injected into the system. The concentration of the polymer in the eluent was monitored using an evaporative light scattering detector. The molecular weights presented in the examples are relative to linear polystyrene standards.

Octene comonomer content in ethylene-octene copolymer samples was determined by infrared spectroscopic analysis. Samples for infrared analysis were prepared by depositing the stabilized polymer solution onto a silanized wafer (Part number 510860, Symyx). By this method, approximately between 0.12 and 0.24 mg of polymer is deposited on the wafer cell. The samples were subsequently analyzed on a Brucker Equinox 55 FTIR spectrometer equipped with Pikes's MappIR specular reflectance sample accessory. Spectra, covering a spectral range of 5000 cm' to 500 cm$^{-1}$, were collected at a 2 cm$^{-1}$ resolution with 32 scans. For ethylene-1-octene copolymers, the wt % comonomer is determined via measurement of the methyl deformation band at ~1375 cm$^{-1}$. The peak height of this band is normalized by the combination and overtone band at ~4321 cm$^{-1}$, which corrects for path length differences. The normalized peak height is correlated to individual calibration curves from $^1$H NMR data to predict the wt % comonomer content within a concentration range of ~2 to 35 wt % for octene. Typically, $R^2$ correlations of 0.98 or greater are achieved.

Differential Scanning calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./minutes and then cooled at a rate of 50° C./min. Melting points were collected during the heating period.

Ethylene Homopolymerization

Quinolinyldiamide complexes (Q1)HfMe$_2$, (Q2)HfMe$_2$, (Q3)HfMe$_2$, and (Q4)HfMe$_2$ were evaluated as catalyst components for the homopolymerization of ethylene. Data for these runs are shown in Table 1. Catalyst activities range from 78-100 kg/mmol Hf/h/bar.

TABLE 1

Ethylene Homopolymerizations*

| run | complex | time (s) | yield (mg) | activity (g/mmol/h/bar) | Mw (g/mol) | Mn (g/mol) | Mw/Mn | Tm-1st (° C.) |
|---|---|---|---|---|---|---|---|---|
| 1 | Q1HfMe2 | 21 | 68 | 83,324 | 334,900 | 189,035 | 1.8 | 137 |
| 2 | Q1HfMe2 | 21 | 60 | 74,283 | 348,963 | 199,653 | 1.7 | 137 |
| 3 | Q2HfMe2 | 20 | 70 | 90,032 | 428,676 | 224,566 | 1.9 | 138 |
| 4 | Q2HfMe2 | 20 | 61 | 79,727 | 322,851 | 172,351 | 1.9 | 137 |
| 5 | Q3HfMe2 | 19 | 68 | 95,440 | 205,750 | 162,518 | 1.3 | 138 |
| 6 | Q3HfMe2 | 17 | 53 | 81,024 | 172,528 | 138,518 | 1.2 | 137 |
| 7 | Q4HfMe2 | 17 | 66 | 100,403 | 243,511 | 170,315 | 1.4 | 138 |
| 8 | Q4HfMe2 | 19 | 55 | 77,996 | 205,127 | 139,196 | 1.5 | 137 |

*Conditions: temperature = 100° C., pressure = 100 psi, 20 nmol complex, uptake = 12 psi, activator = 1.1 molar equivalents [PhNMe$_2$H]B(C$_6$F$_5$)$_4$, solvent = isohexane, volume = 5 mL, scavenger = 500 nmol trioctylaluminum.

Ethylene-Octene Copolymerization

Quinolinyldiamide complexes (Q1)HfMe$_2$, (Q2)HfMe$_2$, (Q3)HfMe$_2$, and (Q4)HfMe$_2$ were evaluated as catalyst components for the copolymerization of ethylene and 1-octene. Data for these runs are shown in Table 2. Each catalyst was used under identical conditions for multiple runs, and significant scatter in the data is evident in the catalyst activities. Catalyst activities range from 45-140 kg/mmol Hf/h/bar. Comonomer incorporation is significant as evidenced by the low melting points (87° C.-92° C.) of the polyethylenes relative to those of the polyethylene homopolymers from Table 1.

for these runs are shown in Table 3. Runs were performed at either 70° C./120 psi or at 100° C./150 psi. Catalyst activities at 70° C. ranged from 167-581 kg/mmol Hf/h, but activities at 100° C. were lower at 10-103 kg/mmol Hf/h. The choice of ligand has a large effect on the activity of the catalyst, with the complex prepared with Q3 ligand being very active at all temperatures. The ligand also has a large effect on the stereoregularity of the polypropylene produced. The complexes prepared using ligands Q2 and Q4 produced polypropylene with higher melting points than the complexes prepared using ligands Q1 and Q3. Increased polypropylene stereoregularity is thought to be due to the steric bulk of the groups in the $R^{13}$ position (e.g., Ph<ortho-tolyl <xylyl) and the dihydro-1H-indenyl J group instead of a phenylmethyl J group ($R^{13}$+J refer to Formulas I and II).

TABLE 2

Ethylene Octene Copolymerization*

| run | complex | time (s) | yield (mg) | activity (g/mmol/h/bar) | Mw (g/mol) | Mn (g/mol) | Mw/Mn | Tm-1st (° C.) |
|---|---|---|---|---|---|---|---|---|
| 9 | Q1HfMe2 | 42 | 88 | 73,409 | 490,981 | 283,741 | 1.7 | 88 |
| 10 | Q1HfMe2 | 24 | 79 | 113,533 | 437,761 | 260,276 | 1.7 | 87 |
| 11 | Q1HfMe2 | 49 | 86 | 61,778 | 507,623 | 310,758 | 1.6 | 87 |
| 12 | Q1HfMe2 | 34 | 75 | 75,666 | 504,253 | 326,225 | 1.5 | 87 |
| 13 | Q2HfMe2 | 44 | 86 | 67,460 | 636,168 | 371,445 | 1.7 | 87 |
| 14 | Q2HfMe2 | 22 | 75 | 120,960 | 522,563 | 289,615 | 1.8 | 91 |
| 15 | Q2HfMe2 | 75 | 96 | 44,565 | 738,235 | 466,239 | 1.6 | 89 |
| 16 | Q2HfMe2 | 22 | 77 | 120,057 | 569,345 | 322,780 | 1.8 | 92 |
| 17 | Q3HfMe2 | 33 | 105 | 109,941 | 311,378 | 231,837 | 1.3 | 92 |
| 18 | Q3HfMe2 | 19 | 78 | 139,701 | 243,839 | 172,468 | 1.4 | 90 |
| 19 | Q3HfMe2 | 26 | 93 | 126,658 | 280,492 | 207,343 | 1.4 | 89 |
| 20 | Q3HfMe2 | 22 | 76 | 118,099 | 236,068 | 169,881 | 1.4 | 90 |
| 21 | Q4HfMe2 | 35 | 100 | 98,342 | 399,009 | 272,499 | 1.5 | 92 |
| 22 | Q4HfMe2 | 29 | 89 | 106,410 | 344,216 | 216,175 | 1.6 | 90 |
| 23 | Q4HfMe2 | 33 | 97 | 102,461 | 383,423 | 238,459 | 1.6 | 90 |
| 24 | Q4HfMe2 | 25 | 81 | 115,589 | 334,455 | 224,620 | 1.5 | 89 |

*Conditions: 0.1 mL 1-octene, temperature = 80° C., pressure = 75 psi, 20 nmol complex, uptake = 12 psi, activator = 1.1 molar equivalents [PhNMe$_2$H]B(C$_6$F$_5$)$_4$, solvent = isohexane, volume = 5 mL, scavenger = 500 nmol trioctylaluminum.

Propylene Homopolymerization

Quinolinyldiamide complexes (Q1)HfMe$_2$, (Q2)HfMe$_2$, (Q3)HfMe$_2$, and (Q4)HfMe$_2$ were evaluated as catalyst components for the homopolymerization of propylene. Data

TABLE 3

Propylene Homopolymerization*

| Run | complex | T (° C.) | P (psi) | time (s) | yield (mg) | activity (kg/mmol/h) | Mw (kg/mol) | Mn (kg/mol) | Mw/Mn | Tm-1st (° C.) |
|---|---|---|---|---|---|---|---|---|---|---|
| 25 | Q1HfMe2 | 70 | 120 | 53 | 250 | 427 | 924 | 459 | 2.0 | 120 |
| 26 | Q1HfMe2 | 70 | 120 | 55 | 239 | 392 | 973 | 563 | 1.7 | 120 |
| 27 | Q1HfMe2 | 100 | 150 | 174 | 101 | 52 | 441 | 221 | 2.0 | 116 |
| 28 | Q1HfMe2 | 100 | 150 | 416 | 82 | 18 | 424 | 199 | 2.1 | 116 |

TABLE 3-continued

Propylene Homopolymerization*

| Run | complex | T (° C.) | P (psi) | time (s) | yield (mg) | activity (kg/mmol/h) | Mw (kg/mol) | Mn (kg/mol) | Mw/Mn | Tm-1st (° C.) |
|---|---|---|---|---|---|---|---|---|---|---|
| 29 | Q2HfMe2 | 70 | 120 | 68 | 189 | 250 | 1,480 | 967 | 1.5 | 140 |
| 30 | Q2HfMe2 | 70 | 120 | 79 | 147 | 167 | 1,562 | 837 | 1.9 | 140 |
| 31 | Q2HfMe2 | 100 | 150 | 635 | 85 | 12 | 602 | 318 | 1.9 | 141 |
| 32 | Q2HfMe2 | 100 | 150 | 745 | 83 | 10 | 632 | 340 | 1.9 | 141 |
| 33 | Q3HfMe2 | 70 | 120 | 42 | 271 | 581 | 764 | 381 | 2.0 | 111 |
| 34 | Q3HfMe2 | 70 | 120 | 40 | 255 | 577 | 761 | 316 | 2.4 | 111 |
| 35 | Q3HfMe2 | 100 | 150 | 110 | 126 | 103 | 305 | 146 | 2.1 | 109 |
| 36 | Q3HfMe2 | 100 | 150 | 114 | 128 | 101 | 312 | 165 | 1.9 | 107 |
| 37 | Q4HfMe2 | 70 | 120 | 49 | 190 | 347 | 662 | 283 | 2.3 | 138 |
| 38 | Q4HfMe2 | 70 | 120 | 44 | 162 | 334 | 646 | 330 | 2.0 | 138 |
| 39 | Q4HfMe2 | 100 | 150 | 374 | 90 | 22 | 339 | 199 | 1.7 | 134 |
| 40 | Q4HfMe2 | 100 | 150 | 354 | 86 | 22 | 332 | 171 | 1.9 | 134 |

*Conditions: 40 nmol complex, uptake = 2 psi for 70° C. runs and 8 for 100° C. runs, activator = 1.1 molar equivalents [PhNMe$_2$H]B(C$_6$F$_5$)$_4$, solvent = isohexane, volume = 5 mL, scavenger = 500 nmol trioctylaluminum.

Additional complexes (CAT-1, CAT-2, and CAT-3) were synthesized and used for ethylene-propylene copolymerizations in a continuous reactor. These were compared with (Q5)HfMe$_2$.

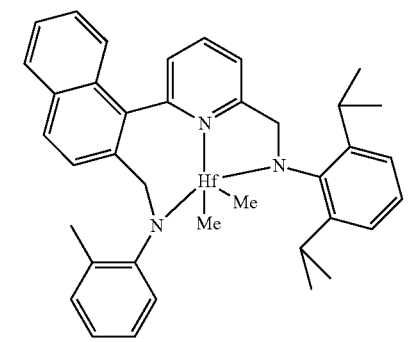

CAT-1

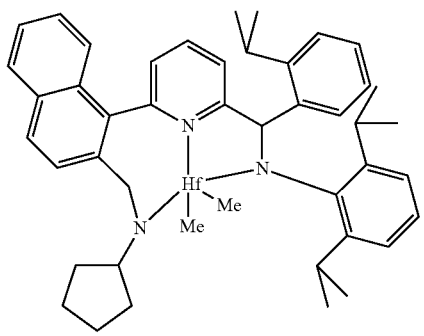

CAT-2

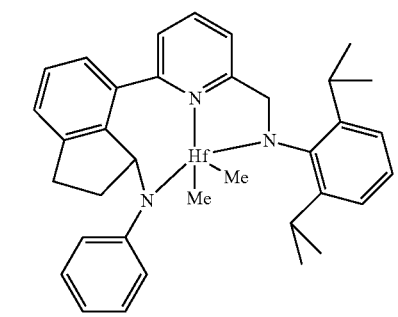

CAT-3

Cat-1 was prepared as described in U.S. Pat. No. 9,102,773. Cat-2 was prepared using the general method described in U.S. Pat. No. 9,315,526. Cat-3 was synthesized according to the procedure described in U.S. Pat. No. 9,290,519.

The following examples were produced using a solution process in a 1 liter continuous stirred-tank reactor (autoclave reactor). A 1-liter Autoclave reactor was equipped with a stirrer, a pressure controller, and a water cooling/steam heating element with a temperature controller. The reactor was operated in liquid fill condition at a reactor pressure in excess of the bubbling point pressure of the reactant mixture, keeping the reactants in liquid phase. Isohexane and propylene were pumped into the reactors by Pulsa feed pumps. All flow rates of liquid were controlled using Coriolis mass flow controller (Quantim series from Brooks). Ethylene and hydrogen flowed as a gas under its own pressure through a Brooks flow controller. Monomers (e.g., ethylene and propylene) and hydrogen feeds were combined into one stream and then mixed with a pre-chilled isohexane stream that had been cooled to at least 0° C. The mixture was then fed to the reactor through a single line. Scavenger solution was also added to the combined solvent and monomer stream just before it entered the reactor to further reduce any catalyst poisons. Similarly, catalyst solution was fed to the reactor using an ISCO syringe pump through a separate line.

The polymer produced in the reactor exited through a back pressure control valve that reduced the pressure to atmospheric. This caused the unconverted monomers in the solution to flash into a vapor phase which was vented from the top of a vapor liquid separator. The liquid phase, comprising mainly polymer and solvent, was collected for polymer recovery. The collected samples were first air-dried in a hood to evaporate most of the solvent, and then dried in a vacuum oven at a temperature of about 90° C. for about 12 hours. The vacuum oven dried samples were weighed to obtain yields.

Catalysts used in these examples were Cat-1, Cat-2, Cat-3 and (Q5)HfMe$_2$. Activator used was N,N-dimethylanilinium tetrakis(perfluorophenyl) borate (BF20). Both the catalyst and activator were first dissolved in toluene and the solutions were kept in an inert atmosphere. The solutions of catalyst and activator were premixed and fed into the reactor using an ISCO™ syringe pump. The catalyst to activator feed ratio (molar) was set at 0.98. Tri-n-octylaluminum (TNOAL) solution (available from Sigma Aldrich, Milwaukee, Wis.) was further diluted in isohexane and used as a scavenger.

Runs 1 through 14 are presented as comparatives. Runs 15 through 28 are inventive.

Specific polymerization process conditions and some characteristic properties are listed in Table A. The scavenger feed rate was adjusted to optimize the catalyst efficiency and the feed rate varied from 0 (no scavenger) to 15 µmol/min. The catalyst feed rates was adjusted according to the level of impurities in the system to reach the targeted conversions listed. All the reactions were carried out at a pressure of about 2.4 MPa/g unless otherwise mentioned. Additional processing conditions for the polymerization process of example 1 to 28, and the properties of the polymers produced are included below in Table A. Ethylene content was determined by FTIR, ASTM D3900. Melt Flow Rate (MFR) was determined according to ASTM 1238 (230° C., 2.16 kg) and are presented as dg polymer/minute.

Runs 15 through 22 demonstrate that the catalyst system (Q5)HfMe$_2$/BF20 produces high molecular weight ethylene-propylene copolymer containing 7.0-16.4% ethylene at 85° C. with productivities of 94 kg polymer/mmol Hf or greater. Under similar process conditions the comparative catalysts had productivities of 55 kg/mmol Hf or less (see runs 3 and 5 through 14).

Runs 25 and 28 demonstrate that (Q5)HfMe$_2$/BF20 produces high molecular weight ethylene-propylene copolymer containing 10-16% ethylene at 100° C. with productivities of 82 kg polymer/mmol Hf or greater. Under similar condition CAT-1/BF20 had a productivity of 19 kg/mmol Hf (see run 4).

TABLE A

Run conditions, results, and polymer characterization data for continuous ethylene-propylene copolymerizations.

| Run | Rxr Temp | C3 (g/min) | C2 (SLPM) | H2 (Scc/min) | isohex, (G/min) | Catalyst | Cat. rate (mol/min) | 25 wt % Oct3Al rate (mol/min) |
|---|---|---|---|---|---|---|---|---|
| 1 | 55 | 14.0 | 0.90 | 0.0 | 56.7 | CAT-1/BF20 | 1.02E−07 | 7.43E−06 |
| 2 | 70 | 14.0 | 0.90 | 0.0 | 56.7 | CAT-1/BF20 | 1.28E−07 | 7.43E−06 |
| 3 | 85 | 14.0 | 0.90 | 0.0 | 56.7 | CAT-1/BF20 | 1.70E−07 | 7.43E−06 |
| 4 | 100 | 14.0 | 0.90 | 0.0 | 56.7 | CAT-1/BF20 | 2.56E−07 | 7.43E−06 |
| 5 | 85 | 14.0 | 0.40 | 2.4 | 54.0 | CAT-2/BF20 | 1.63E−07 | 5.50E−06 |
| 6 | 85 | 14.0 | 0.60 | 2.4 | 54.0 | CAT-2/BF20 | 1.52E−07 | 5.50E−06 |
| 7 | 85 | 14.0 | 0.80 | 2.4 | 54.0 | CAT-2/BF20 | 1.42E−07 | 5.50E−06 |
| 8 | 85 | 14.0 | 1.00 | 2.4 | 54.0 | CAT-2/BF20 | 1.31E−07 | 5.50E−06 |
| 9 | 85 | 14.0 | 1.20 | 2.4 | 54.0 | CAT-2/BF20 | 1.20E−07 | 5.50E−06 |
| 10 | 85 | 14.0 | 0.40 | 2.4 | 56.0 | CAT-3/BF20 | 1.43E−07 | 5.50E−06 |
| 11 | 85 | 14.0 | 0.60 | 2.4 | 56.0 | CAT-3/BF20 | 1.43E−07 | 5.50E−06 |
| 12 | 85 | 14.0 | 0.80 | 2.4 | 56.0 | CAT-3/BF20 | 1.43E−07 | 5.50E−06 |
| 13 | 85 | 14.0 | 1.00 | 2.4 | 56.0 | CAT-3/BF20 | 1.43E−07 | 5.50E−06 |
| 14 | 85 | 14.0 | 1.20 | 2.4 | 56.0 | CAT-3/BF20 | 1.43E−07 | 5.50E−06 |
| 15 | 85 | 14.0 | 0.40 | 2.4 | 54.0 | (Q5)HfMe2/BF20 | 8.25E−08 | 5.50E−06 |
| 16 | 85 | 14.0 | 0.60 | 2.4 | 54.0 | (Q5)HfMe2/BF20 | 7.71E−08 | 5.50E−06 |
| 17 | 85 | 14.0 | 0.80 | 2.4 | 54.0 | (Q5)HfMe2/BF20 | 7.16E−08 | 5.50E−06 |
| 18 | 85 | 14.0 | 0.80 | 0.0 | 54.0 | (Q5)HfMe2/BF20 | 7.16E−08 | 5.50E−06 |
| 19 | 85 | 14.0 | 1.00 | 2.4 | 54.0 | (Q5)HfMe2/BF20 | 6.62E−08 | 5.50E−06 |
| 20 | 85 | 14.0 | 1.00 | 2.4 | 56.7 | (Q5)HfMe2/BF20 | 6.07E−08 | 7.43E−06 |
| 21 | 85 | 14.0 | 1.00 | 2.4 | 55.0 | (Q5)HfMe2/BF20 | 6.07E−08 | 2.75E−06 |
| 22 | 85 | 14.0 | 1.20 | 2.4 | 54.0 | (Q5)HfMe2/BF20 | 6.07E−08 | 5.50E−06 |
| 23 | 90 | 14.0 | 1.20 | 2.4 | 56.7 | (Q5)HfMe2/BF20 | 6.07E−08 | 7.43E−06 |
| 24 | 95 | 14.0 | 1.20 | 2.4 | 56.7 | (Q5)HfMe2/BF20 | 6.62E−08 | 7.43E−06 |
| 25 | 100 | 14.0 | 1.20 | 2.4 | 56.7 | (Q5)HfMe2/BF20 | 7.16E−08 | 7.43E−06 |
| 26 | 90 | 14.0 | 0.60 | 2.4 | 56.7 | (Q5)HfMe2/BF20 | 7.89E−08 | 7.43E−06 |
| 27 | 95 | 14.0 | 0.60 | 2.4 | 56.7 | (Q5)HfMe2/BF20 | 8.25E−08 | 7.43E−06 |
| 28 | 100 | 14.0 | 0.60 | 2.4 | 56.7 | (Q5)HfMe2/BF20 | 8.50E−08 | 7.43E−06 |

| Run | Collection time (min) | Polymer made (gram) | Monomers conversion (%) | Productivity (g/mmol Hf) | C2 wt % IR (*HNMR) | MFR 2.16 kg 23° C. |
|---|---|---|---|---|---|---|
| 1 | 20 | 106 | 35% | 51,714 | 18.9%* | <0.1 |
| 2 | 30 | 174 | 38% | 45,218 | 17.8%* | <0.1 |
| 3 | 30 | 187 | 41% | 36,684 | 16.3%* | <0.1 |
| 4 | 30 | 145 | 32% | 18,901 | 19%* | <0.1 |
| 5 | 40 | 177 | 31% | 27,082 | 7.4% | 0.7 |
| 6 | 40 | 204 | 35% | 33,497 | 10.4% | 0.5 |
| 7 | 40 | 154 | 26% | 27,279 | 19.6% | 0.2 |
| 8 | 40 | 170 | 28% | 32,594 | 23.4% | 0.2 |
| 9 | 40 | 197 | 32% | 41,152 | 25.0% | 0.2 |
| 10 | 40 | 279 | 48% | 48,709 | 5.3% | 8.1 |
| 11 | 40 | 287 | 49% | 50,017 | 8.3% | 5.1 |
| 12 | 40 | 297 | 50% | 51,745 | 11.0% | 3.9 |
| 13 | 40 | 305 | 51% | 53,280 | 13.3% | 1.8 |
| 14 | 40 | 313 | 51% | 54,676 | 16.1% | 1.1 |
| 15 | 40 | 310 | 54% | 93,954 | 7.2% | 0.6 |
| 16 | 40 | 329 | 56% | 106,642 | 9.0% | 0.5 |
| 17 | 40 | 294 | 49% | 102,590 | 11.1% | 0.4 |
| 18 | 40 | 281 | 47% | 98,017 | 11.6% | 0.1 |
| 19 | 40 | 309 | 51% | 116,704 | 13.4% | 0.2 |
| 20 | 20 | 166 | 55% | 136,925 | 12.3% | 0.5 |
| 21 | 20 | 162 | 54% | 133,383 | 12.4% | 0.2 |
| 22 | 40 | 302 | 49% | 124,403 | 16.4% | 0.0 |

TABLE A-continued

Run conditions, results, and polymer characterization data for continuous ethylene-propylene copolymerizations.

| | | | | | | |
|---|---|---|---|---|---|---|
| 23 | 40 | 327 | 53% | 134,660 | 14.9% | |
| 24 | 40 | 375 | 61% | 141,610 | 15.0% | 0.2 |
| 25 | 40 | 314 | 51% | 109,641 | 15.6% | 0.2 |
| 26 | 40 | 317 | 54% | 100,539 | 7.1% | 0.2 |
| 27 | 40 | 299 | 51% | 90,502 | 7.3% | 0.3 |
| 28 | 40 | 277 | 47% | 81,558 | 9.8% | 0.6 |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element, or a group of elements is preceded with the transitional phrase "comprising," it is understood that we also contemplate the same composition or group of elements with transitional phrases "consisting essentially of," "consisting of," "selected from the group consisting of," or "is" preceding the recitation of the composition, element, or elements and vice versa.

What is claimed is:

1. A quinolinyldiamido transition metal complex represented by Formula I:

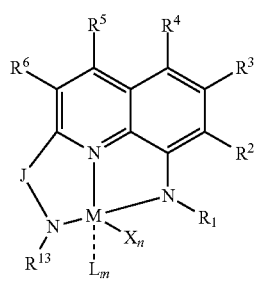

(I)

wherein:
M is a Group 3, 4, 5, 6, 7, 8, 9, 10, 11, or 12 metal;
J is a three-atom-length bridge between the quinoline and the amido nitrogen;
X is an anionic leaving group;
L is a neutral Lewis base;
$R^1$ and $R^{13}$ are independently selected from the group consisting of hydrocarbyls, substituted hydrocarbyls, and silyl groups;
$R^2$, $R^3$, $R^4$, $R^5$, and $R^6$ are independently selected from the group consisting of hydrogen, hydrocarbyls, alkoxy, silyl, amino, aryloxy, substituted hydrocarbyls, halogen, and phosphino;
n is 1 or 2;
m is 0, 1, or 2;
n+m is not greater than 4; and
any two adjacent R groups (e.g., $R^1$ & $R^2$, $R^2$ & $R^3$, etc.) may be joined to form a substituted hydrocarbyl, unsubstituted hydrocarbyl, substituted heterocyclic ring, or unsubstituted heterocyclic ring, where the ring has 5, 6, 7, or 8 ring atoms and where substitutions on the ring can join to form additional rings;
any two X groups may be joined together to form a dianionic group;
any two L groups may be joined together to form a bidentate Lewis base; and
an X group may be joined to an L group to form a monoanionic bidentate group.

2. The complex of claim 1, wherein J is selected from the following structures:

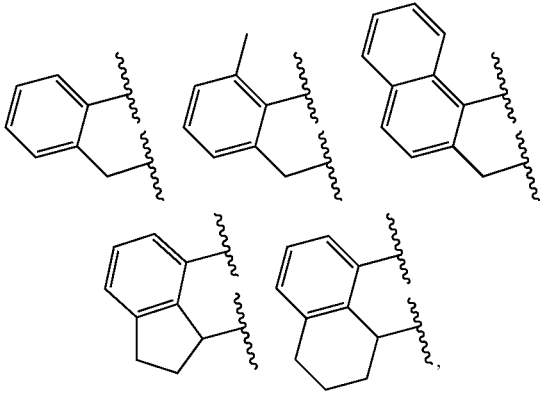

where ⸺ indicates connection to the complex.

3. The complex of claim 1, wherein the complex is further represented by Formula (II):

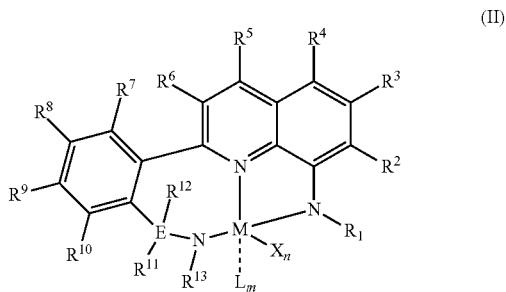

(II)

wherein M, L, X, m, n, $R^1$, $R^2$, $R^3$, $R^4$, $R^5$, $R^6$, and $R^{13}$ are as defined in claim 1, and
E is carbon, silicon, or germanium;
$R^7$ through $R^{12}$ are independently selected from the group consisting of hydrogen, hydrocarbyls, alkoxy, silyl, amino, aryloxy, substituted hydrocarbyls, halogen, and
any two R groups may be joined to form a substituted or unsubstituted hydrocarbyl or heterocyclic ring, where the ring has 5, 6, 7, or 8 ring atoms and where substitutions on the ring can join to form additional rings.

4. The complex of claim 3, wherein $R^{11}$ and $R^{12}$ are independently selected from hydrogen, methyl, ethyl, phenyl, isopropyl, isobutyl, and trimethylsilyl.

5. The complex of claim 3, wherein E is carbon.

6. The complex of claim 3, wherein $R^7$, $R^8$, $R^9$, and $R^{10}$ are independently selected from hydrogen, methyl, ethyl, propyl, isopropyl, phenyl, cyclohexyl, fluoro, chloro, methoxy, ethoxy, phenoxy, and trimethylsilyl.

7. The complex of claim 1, wherein M is Ti, Zr, or Hf.

8. The complex of claim 6, wherein M is Ti, Zr, or Hf.

9. The complex of claim 1, wherein $R^2$, $R^3$, $R^4$, $R^5$, and $R^6$ are independently selected from the group consisting of hydrogen, hydrocarbyls, alkoxy, silyl, amino, substituted hydrocarbyls, and halogen.

10. The complex of claim 3, wherein $R^2$, $R^3$, $R^4$, $R^5$, and $R^6$ are independently selected from the group consisting of hydrogen, hydrocarbyls, alkoxy, silyl, amino, substituted hydrocarbyls, and halogen.

11. The complex of claim 1, wherein each L is independently selected from $Et_2O$, MeOtBu, $Et_3N$, $PhNMe_2$, $MePh_2N$, tetrahydrofuran, and dimethylsulfide.

12. The complex of claim 3, wherein each L is independently selected from $Et_2O$, MeOtBu, $Et_3N$, $PhNMe_2$, $MePh_2N$, tetrahydrofuran, and dimethylsulfide.

13. The complex of claim 1, wherein each X is independently selected from methyl, benzyl, trimethylsilyl, neopentyl, ethyl, propyl, butyl, phenyl, hydrido, chloro, fluoro, bromo, iodo, dimethylamido, diethylamido, dipropylamido, and diisopropylamido.

14. The complex of claim 3, wherein each X is independently selected from methyl, benzyl, trimethylsilyl, neopentyl, ethyl, propyl, butyl, phenyl, hydrido, chloro, fluoro, bromo, iodo, dimethylamido, diethylamido, dipropylamido, and diisopropylamido.

15. The complex of claim 1, wherein IV is 2,6-diisopropylphenyl, 2,4,6-triisopropylphenyl, 2,6-diisopropyl-4-methylphenyl, 2,6-diethylphenyl, 2-ethyl-6-isopropylphenyl, 2,6-bis(3-pentyl)phenyl, 2,6-dicyclopentylphenyl, or 2,6-dicyclohexylphenyl.

16. The complex of claim 3, wherein IV is 2,6-diisopropylphenyl, 2,4,6-triisopropylphenyl, 2,6-diisopropyl-4-methylphenyl, 2,6-diethylphenyl, 2-ethyl-6-isopropylphenyl, 2,6-bis(3-pentyl)phenyl, 2,6-dicyclopentylphenyl, or 2,6-dicyclohexylphenyl.

17. The complex of claim 1, wherein $R^{13}$ is phenyl, 2-methylphenyl, 2-ethylphenyl, 2-propylphenyl, 2,6-dimethylphenyl, 2-isopropylphenyl, 4-methylphenyl, 3,5-dimethylphenyl, 3,5-di-tert-butylphenyl, 4-fluorophenyl, 3-methylphenyl, 4-dimethylaminophenyl, or 2-phenylphenyl.

18. The complex of claim 3, wherein $R^{13}$ is phenyl, 2-methylphenyl, 2-ethylphenyl, 2-propylphenyl, 2,6-dimethylphenyl, 2-isopropylphenyl, 4-methylphenyl, 3,5-dimethylphenyl, 3,5-di-tert-butylphenyl, 4-fluorophenyl, 3-methylphenyl, 4-dimethylaminophenyl, or 2-phenylphenyl.

19. The complex of claim 1, wherein J is dihydro-1H-indenyl and $R^1$ is 2,6-dialkylphenyl or 2,4,6-trialkylphenyl.

20. The complex of claim 1, wherein $R^1$ is 2,6-diisopropylphenyl and $R^{13}$ is a hydrocarbyl group containing 1, 2, 3, 4, 5, 6, or 7 carbon atoms.

21. The complex of claim 3, wherein $R^1$ is 2,6-diisopropylphenyl and $R^{13}$ is a hydrocarbyl group containing 1, 2, 3, 4, 5, 6, or 7 carbon atoms.

22. The complex of claim 3, wherein $R^{10}$ and $R^{11}$ are joined to form a substituted or unsubstituted hydrocarbyl or heterocyclic ring, where the ring has 5, 6, 7, or 8 ring atoms and where substitutions on the ring can join to form additional rings.

23. The complex of claim 3, wherein $R^{10}$ and $R^{11}$ are joined to form a substituted or unsubstituted saturated hydrocarbyl ring, where the ring has 6 ring atoms and where substitutions on the ring can join to form additional rings.

24. The complex of claim 1, wherein the complex is further represented by Formula:

wherein M, L, X, m, n, $R^1$, $R^2$, $R^3$, $R^4$, $R^5$, $R^6$, and $R^{13}$ are as defined in claim 1;

$R^7$ through $R^{12}$ and $R^{14}$ are independently selected from the group consisting of hydrogen, hydrocarbyls, alkoxy, silyl, amino, aryloxy, substituted hydrocarbyls, halogen, and any two R groups may be joined to form a substituted or unsubstituted hydrocarbyl or heterocyclic ring, where the ring has 5, 6, 7, or 8 ring atoms and where substitutions on the ring can join to form additional rings.

25. A quinolinyldiamido transition metal complex represented by Formula:

26. A catalyst system comprising an activator and the transition metal complex of claim 1.

27. The catalyst system of claim 26, wherein two or more catalyst complexes are present.

28. The catalyst system of claim 26, wherein the activator is an alumoxane.

29. The catalyst system of claim 26, wherein the activator is a non-coordinating anion.

30. The catalyst system of claim 26, wherein the catalyst complex and/or the activator is supported.

31. A polymerization process to produce polyolefin comprising contacting one or more olefin monomers with the catalyst system of claim 26 and obtaining olefin polymer.

32. A polymerization process to produce polyolefin comprising contacting, in solution phase, one or more olefin monomers with a catalyst system comprising the complex of claim 25 and activator, at a temperature of at least 85° C., and obtaining olefin polymer, where the olefin monomers comprise ethylene and propylene.

33. The process of claim 31, wherein the monomers comprise ethylene.

34. The process of claim 31, wherein the monomers comprise propylene.

35. The process of claim 31, wherein the polymerization process is a solution process.

36. The process of claim 31, wherein the polyolefin produced is an ethylene polymer.

37. The process of claim 34, wherein the polyolefin produced is isotactic polypropylene.

38. A catalyst system comprising the activator and the transition metal complex of claim 3.

39. The catalyst system of claim 26, wherein M=Hf, Zr, or Ti.

40. The catalyst system of claim 38, wherein M=Hf, Zr, or Ti.

41. The catalyst system of claim 26, wherein:

$R^2, R^3, R^4, R^5$, and $R^6$ are independently selected from the group consisting of hydrogen, hydrocarbyls, alkoxy, silyl, amino, substituted hydrocarbyls, and halogen;

$R^1$ is 2,6-diisopropylphenyl, 2,4,6-triisopropylphenyl, 2,6-diisopropyl-4-methylphenyl, 2,6-diethylphenyl, 2-ethyl-6-isopropylphenyl, 2,6-bis(3-pentyl)phenyl, 2,6-dicyclopentylphenyl, or 2,6-dicyclohexylphenyl;

$R^{13}$ is phenyl, 2-methylphenyl, 2-ethylphenyl, 2-propylphenyl, 2,6-dimethylphenyl, 2-isopropylphenyl, 4-methylphenyl, 3,5-dimethylphenyl, 3,5-di-tert-butylphenyl, 4-fluorophenyl, 3-methylphenyl, 4-dimethylaminophenyl, or 2-phenylphenyl;

$R^{13}$ is phenyl, 2-methylphenyl, 2-ethylphenyl, 2-propylphenyl, 2,6-dimethylphenyl, 2-isopropylphenyl, 4-methylphenyl, 3,5-dimethylphenyl, 3,5-di-tert-butylphenyl, 4-fluorophenyl, 3-methylphenyl, 4-dimethylaminophenyl, or 2-phenylphenyl;

J is selected from the following structures:

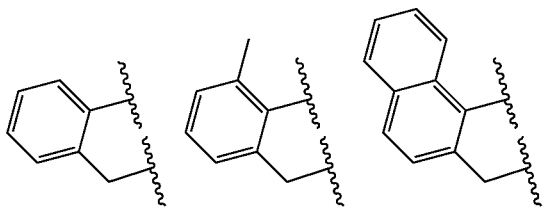

-continued

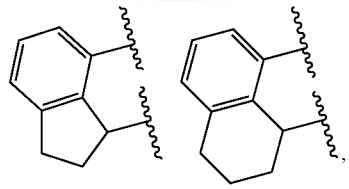

where ⌇ indicates connection to the complex; and

M is Ti, Zr, or Hf.

42. The catalyst system of 38, wherein:

$R^2, R^3, R^4, R^5$, and $R^6$ are independently selected from the group consisting of hydrogen, hydrocarbyls, alkoxy, silyl, amino, substituted hydrocarbyls, and halogen;

$R^1$ is 2,6-diisopropylphenyl, 2,4,6-triisopropylphenyl, 2,6-diisopropyl-4-methylphenyl, 2,6-diethylphenyl, 2-ethyl-6-isopropylphenyl, 2,6-bis(3-pentyl)phenyl, 2,6-dicyclopentylphenyl, or 2,6-dicyclohexylphenyl;

$R^{13}$ is phenyl, 2-methylphenyl, 2-ethylphenyl, 2-propylphenyl, 2,6-dimethylphenyl, 2-isopropylphenyl, 4-methylphenyl, 3,5-dimethylphenyl, 3,5-di-tert-butylphenyl, 4-fluorophenyl, 3-methylphenyl, 4-dimethylaminophenyl, or 2-phenylphenyl;

$R^{11}$ and $R^{12}$ are independently selected from hydrogen, methyl, ethyl, phenyl, isopropyl, isobutyl, and trimethylsilyl;

E is carbon;

$R^7, R^8, R^9$, and $R^{10}$ are independently selected from hydrogen, methyl, ethyl, propyl, isopropyl, phenyl, cyclohexyl, fluoro, chloro, methoxy, ethoxy, phenoxy, and trimethylsilyl; and M is Ti, Zr, or Hf.

43. A polymerization process to produce olefin comprising contacting, in solution phase, one or more olefin monomers with a catalyst system comprising the complex of claim 25 and activator, at a temperature of at least 85° C., and obtaining olefin polymer, where the olefin monomers comprise ethylene and propylene and the olefin polymer has a melt flow rate (230° C., 2.16 kg) of less than 1.0 dg/min.

44. The polymerization process of claim 32, wherein the activator is a non-coordinating anion.

* * * * *

UNITED STATES PATENT AND TRADEMARK OFFICE
CERTIFICATE OF CORRECTION

PATENT NO. : 10,208,140 B2  
APPLICATION NO. : 15/629586  
DATED : February 19, 2019  
INVENTOR(S) : John R. Hagadorn et al.

It is certified that error appears in the above-identified patent and that said Letters Patent is hereby corrected as shown below:

In the Claims

In Claim 41 at Column 43, Lines 28-32, please delete "$R^{13}$ is phenyl, 2-methylphenyl, 2-ethylphenyl, 2-propylphenyl, 2,6-dimethylphenyl, 2-isopropylphenyl, 4-methylphenyl, 3,5-dimethylphenyl, 3,5-di-tert-butylphenyl, 4-fluorophenyl, 3-methylphenyl, 4-dimethylaminophenyl, or 2-phenylphenyl;".

Signed and Sealed this  
Twenty-sixth Day of March, 2019

Andrei Iancu  
*Director of the United States Patent and Trademark Office*